(12) United States Patent
Bublewitz et al.

(10) Patent No.: US 9,381,140 B2
(45) Date of Patent: Jul. 5, 2016

(54) RADICALLY POLYMERISABLE DENTAL MATERIAL, CURED PRODUCT AND USAGE

(71) Applicant: Kettenbach GmbH & Co. KG, Eschenburg (DE)

(72) Inventors: Alexander Bublewitz, Herborn (DE); Jens-Peter Reber, Meinerzhagen (DE); Alexander Theis, Eschenburg (DE)

(73) Assignee: Kettenbach GmbH & Co. KG, Eschenburg (DE)

( * ) Notice: Subject to any disclaimer, the term of this patent is extended or adjusted under 35 U.S.C. 154(b) by 0 days.

(21) Appl. No.: 14/424,729

(22) PCT Filed: Aug. 30, 2013

(86) PCT No.: PCT/EP2013/068030
§ 371 (c)(1),
(2) Date: Feb. 27, 2015

(87) PCT Pub. No.: WO2014/033280
PCT Pub. Date: Mar. 6, 2014

(65) Prior Publication Data
US 2015/0231041 A1    Aug. 20, 2015

(30) Foreign Application Priority Data

Aug. 31, 2012 (DE) .......................... 10 2012 017 197

(51) Int. Cl.
| | |
|---|---|
| C08F 2/46 | (2006.01) |
| C08J 3/28 | (2006.01) |
| C08F 2/50 | (2006.01) |
| C08G 61/04 | (2006.01) |
| A61K 6/083 | (2006.01) |
| A61K 6/00 | (2006.01) |

(52) U.S. Cl.
CPC ............. *A61K 6/0835* (2013.01); *A61K 6/0088* (2013.01)

(58) Field of Classification Search
None
See application file for complete search history.

(56) References Cited

U.S. PATENT DOCUMENTS

| | | | |
|---|---|---|---|
| 3,006,112 | A | 10/1961 | Rowe |
| 4,629,746 | A | 12/1986 | Michl et al. |
| 4,906,446 | A | 3/1990 | Engelbrecht et al. |
| 5,009,597 | A | 4/1991 | Schaefer |
| 5,228,907 | A | 7/1993 | Eppinger et al. |
| 5,708,051 | A | 1/1998 | Erdrich et al. |
| 5,852,096 | A | 12/1998 | Heindl et al. |
| 5,990,195 | A | 11/1999 | Arita |
| 6,300,389 | B1 | 10/2001 | Sato et al. |
| 6,426,373 | B1 | 7/2002 | Stange et al. |
| 6,593,395 | B2 | 7/2003 | Angeletakis et al. |
| 6,652,281 | B1 | 11/2003 | Eckhardt et al. |
| 6,730,156 | B1 | 5/2004 | Windisch et al. |
| 6,936,006 | B2 | 8/2005 | Sabra |
| 6,936,652 | B2 | 8/2005 | van Bennekom et al. |
| 7,601,767 | B2 | 10/2009 | Ruppert et al. |
| 7,820,733 | B2 | 10/2010 | Ohara |
| 8,686,061 | B2 | 4/2014 | Neffgen et al. |
| 2003/0134932 | A1 * | 7/2003 | Lehmann ............... A61K 6/083 523/113 |
| 2005/0234148 | A1 | 10/2005 | Ruppert et al. |
| 2005/0260151 | A1 | 11/2005 | Pays et al. |
| 2006/0229377 | A1 | 10/2006 | Bublewitz et al. |
| 2008/0167399 | A1 | 7/2008 | Utterodt et al. |
| 2009/0003565 | A1 | 1/2009 | Kasamatsu |
| 2010/0292363 | A1 | 11/2010 | Neffgen et al. |
| 2013/0225699 | A1 * | 8/2013 | Bublewitz ............ A61K 6/0017 514/772.4 |

FOREIGN PATENT DOCUMENTS

| | | |
|---|---|---|
| DE | 2816823 A1 | 10/1978 |
| DE | 3502594 A1 | 7/1986 |
| DE | 4001977 A1 | 8/1991 |
| DE | 4110612 A1 | 5/1992 |
| DE | 4412831 A1 | 10/1995 |
| DE | 4446033 A1 | 6/1996 |
| DE | 19615763 A1 | 10/1997 |
| DE | 19823530 A1 | 12/1998 |
| DE | 19901783 A1 | 7/1999 |
| DE | 19848886 A1 | 5/2000 |
| DE | 19904816 A1 | 9/2000 |
| DE | 19919581 A1 | 11/2000 |
| DE | 19961341 A1 | 6/2001 |
| DE | 102004010220 A1 | 9/2004 |
| DE | 102004017562 A1 | 11/2005 |
| DE | 102005016762 A1 | 10/2006 |
| DE | 102009006173 A1 | 7/2010 |
| DE | 102009058638 A1 | 6/2011 |
| DE | 102010046697 A1 | 3/2012 |

(Continued)

OTHER PUBLICATIONS

Form PCT/IB/338, Notification of Transmittal of Translation of the International Preliminary Report on Patentability.

*Primary Examiner* — Ling Choi
*Assistant Examiner* — Jessica E Whiteley
(74) *Attorney, Agent, or Firm* — McDonnell Boehnen Hulbert & Berghoff LLP

(57) ABSTRACT

The invention relates to a polymerizable dental material containing a) at least one curable aliphatic and/or cycloaliphatic monomer system having a refractive index that is measured at 23° C. and a wavelength of 589 nm of less than or equal to 1.50 that contains at least one aliphatic and/or cycloaliphatic bis(meth)acrylate and/or at least one aliphatic and/or cycloaliphatic bis(meth)acrylamide; and b) 15 to 80% by weight relative to the total mass of the dental material of at least one filler selected from the group of fused silica having a refractive index that is measured at 23° C. and a wavelength of 589 nm of 1.45 to 1.47, or cristobalite with a refractive index that is measured at 23° C. and a wavelength of 589 nm of 1.48 to 1.49, or combinations thereof. The radically polymerizable dental material has excellent storage properties and is formulated, in particular, as a two-component mixture containing components A and B. Subsequent to mixing components A and B, the polymerizable mixture cures quickly in the conditions present in the mouth and forms cured masses having outstanding mechanical and optical properties. The cured products can be used, in particular, for producing crowns and bridge material and as core buildup material.

29 Claims, No Drawings

(56) References Cited

FOREIGN PATENT DOCUMENTS

| | | |
|---|---|---|
| EP | 0315186 A2 | 5/1989 |
| EP | 0803240 A2 | 10/1997 |
| EP | 1396256 A2 | 3/2004 |
| EP | 1532958 A1 | 5/2005 |
| EP | 1719497 A1 | 11/2006 |
| EP | 1935393 A2 | 6/2008 |
| EP | 0971678 B9 | 7/2010 |
| EP | 2237763 B1 | 5/2013 |
| GB | 1576080 | 10/1980 |
| WO | 01/10335 * | 2/2001 |
| WO | 0130304 A1 | 5/2001 |
| WO | 03063804 A1 | 8/2003 |
| WO | 2012-052249 * | 4/2012 |

* cited by examiner

RADICALLY POLYMERISABLE DENTAL MATERIAL, CURED PRODUCT AND USAGE

CROSS REFERENCE TO RELATED APPLICATIONS

The present application is a 35 U.S.C. 371 National Application of PCT/EP2013/068030 filed Aug. 30, 2013, which claims priority to German Patent Application No. 10 2012 017 197.8, filed Aug. 31, 2012, the entire contents of which are incorporated entirely herein by reference.

The present invention relates to a radically polymerizable dental material that is advantageously present in the form of a pasty multicomponent formulation containing a selected polymerizable system and a selected filler material or a selected filler material combination. The invention further relates to a polymerizable dental material and to the applications of the polymerizable and the polymerized dental material, preferably as a highly esthetic crown and bridge material, core buildup material, as block and disc material for millable CAD-CAM restorations, or as esthetic cement.

Such polymerizable crown and bridge materials are used, just like millable CAD-CAM restorations, to produce, for example, temporary and definitive, permanent multipart bridges, crowns, inlays, onlays or provisional pins subsequent to endodontic treatment. Core buildup materials are used to restore severely damaged teeth and to secure root pins and esthetic cements, among other things, they are used to secure crowns, bridges, inlays, onlays and veneers.

Generic polymerizable dental materials as such are known in prior art. They contain polymerizable monomers whose polymerization is triggered by radicals that are formed. As a rule, these radicals are formed by the reaction generated by a suitable initiator with a co-initiator, whereby the radical formation starts directly after they are combined. By itself, the initiator has adequate storage stability only at room temperature and it must therefore be stored separately from the co-initiator when the dental materials are stored. Consequently, most of the time, multicomponent systems are used, the components of which are brought into contact with each other only directly prior to processing the dental material and are then carefully mixed.

Particularly in the case of core build-up materials and esthetic cements, light-curing is also desired in addition to the chemical curing after the components have been combined. For this purpose, one or both pastes are provided with an additional photoinitiator that gives dental staff an opportunity for hardening ahead of schedule by using a treatment lamp at any time. Customarily, photoinitiator systems consisting of camphor quinone and an aromatic amine are used for light-curing of dental materials. Upon exposure to blue light having a wave length in the range of 470 nm, such a mixture generates radicals that harden the material completely in less than a minute.

Many requirements are tied to the properties of cured dental materials. Thus, the cured material is intended to come as close as possible to a natural tooth regarding color and translucency. Moreover, the cured material is expected to be able to withstand the chemical conditions in the oral cavity for a long period of time and the mechanical properties such as flexural strength, resistance to pressure and tensile strength, the modulus of elasticity and where required, the resistance to abrasion, must also be selected optimally for the desired purpose of the application.

The curable material should also have sufficient storage stability prior to being processed even under unfavorable ambient conditions for pressure, humidity and temperature and on the other hand, harden quickly inside the mouth upon processing at room temperature. Moreover, the cured molds must be able to be finished, for example, by trimming or milling.

The person skilled in the art has various properties at his disposal to select this property profile. In this way, the mechanical properties can be influenced primarily by the selection of the fillers used. Thereby, among other things, their type and grain size or the grain size distribution of the fillers can play a role. The translucency of the cured product can be influenced in a positive way by the selection of ingredients, or by components with refractive indices that are as similar as possible. For selecting the color of a cured product, the person skilled in the art can select between various colorants and pigments. Even the selection of the monomer system and the type of the initiator system can influence the cured product. Finally, the type of storage can also play a role. The material combinations that are present in the individual components in order to prevent premature polymerization or deactivation of catalysts and catalyst components is an important factor in the conventionally used two-component system.

In addition to the monomers used in the production of the polymerized dental material, the fillers used are of primary importance relative to the dental material's appearance and function. The type and amount of the fillers used influence, among other things, the mechanical properties of the polymerized material as well as its color or translucency. An important criterion of fillers is their BET surface area that primarily determines the overall percentage of filler in the composite matrix at a specified reference viscosity. It in turn influences further important composite properties such as, for example, the volume shrinkage and the heat of reaction while hardening as they are defined within a class of monomers, e.g. (meth)acrylate, by the number of the reactive groups per volume element respectively. Fillers for dental materials are known, for example, from DE 196 15 763 A1, DE 600 30 753 T2 and DE 10 2004 017 562 A1.

Curable dental materials have already been described in detail in prior art. Examples of such materials can be found in DE 198 23 530 B4, DE 199 19 581 A1, DE 44 46 033 A1, DE 41 10 612 A1, DE 40 01 977 A1, DE 10 2007 034 457 A1, DE 10 2005 016 762 A1, DE 199 61 341 C2, DE 198 48 886 A1, DE 10 2009 006 173 A1, DE 10 2009 058 638 A1, DE 10 2010 046 697 A1, DE 199 04 816 A1, U.S. Pat. No. 6,730,156 B1, EP 1 227 781 B1, EP 1 586 294 B1, EP 1 225 867 B1, EP 0 803 240 B1, DE 196 179 31 CI, U.S. Pat. No. 6,593,395 B2, WO 01/30 304 A1, EP 147 187 5, WO 03/063804 A1, EP 15 32 958 A1, EP 1 396 254 A1, EP 0 971 678 B9, DE 10 2004 010 220 A1, EP 03 15 186 B1, U.S. Pat. No. 3,006,112, U.S. Pat. No. 7,820,733 B2, and EP 2 237 763 B1, to name only a few.

Artificial teeth, as well as plastic tooth replacement parts consisting of a core and a casing are known from DE 44 12 831 A1, DE 37 08 618 A1 and DE 38 26 233 C1.

Acrylates and/or methacrylates (herein also referred to as "(meth)acrylates" are used in many curable dental masses as polymerizable components. These are frequently combined with so-called X-ray-opaque dental glasses as filler that has a refractive index in the range of 1.5 to 1.83. If a cured material is required to have good translucency such as, for example, in the case of artificial teeth, the refractive indices of the components of the curable mixture must be selected in such a way that these agree as much as possible. In the conventionally used aromatic or BPA-containing acrylates and/or methacrylates such as, for example, bis-GMA and ethoxylated Bisphenol A dimethacrylate, a very good agreement of the refractive indices can be achieved with X-ray-opaque dental glasses having a refractive index between 1.52 and 1.55, as a result of which translucent, highly esthetic composites can be obtained.

The use of monomers containing BPA as a component has recently become an increasingly discussed subject matter. In various publications (see, e.g.: Bisphenol A—Bulk Chemical with Undesired Side Effects [Bisphenol A—Massenchemikalie mit unerwünschten Nebenwirkungen] at http://www.umweltbundesamt.de/uba-info-medien/mysql_medien.php?anfrage=Kennummer&Suchwort=3782, Bisphenol A (BPA): Use in Food Contact Application at http://www.fda.gov/NewsEvents/PublicHealthFocus/ucm064437.htm or Health Canada's Updated Assessment of Bisphenol A (BPA) Exposure from Food Sources at http://www.hcsc.gc.cafin-an/securit/packag-emball/bpa/bpa_hra-ers-2012-09-eng.php). it is being reported that these types of products can cause serious damage to health because Bisphenol A has an estrogenic effect. As these monomers are produced from Bisphenol A, they usually also contain free Bisphenol A as residue. Because substances analogous to hormones—just like the hormones themselves—affect the body even in low doses, even traces of BPA are classified as being harmful to health.

In dental materials, monomers based on Bisphenol A ensure a sufficiently high degree of hardness, but mostly, this hardness is also connected with an undesirable brittleness that leads to a decreased level of resistance to impact. But a high degree of resistance to impact is an important quality criterion because it is a critical contributor for reducing the susceptibility of breakage of these materials. In EP 1 237 525 B1, various attempts are being described to further reduce the susceptibility of breakage. In addition to integrating polymers and the use of plasticizers, it includes the use of high-molecular, low functioning monomers such as polyethylene glycol diacrylate, which, although it improves the susceptibility of breakage, it severely lowers the mechanical properties and leads to a significant rise in temperature during the curing and therefore cannot be used in applications in the mouth. To solve these problems, EP 1 237 525 B1 describes a composite that contains at least two urethane(meth)acrylates that have a different molecular weight. But the urethane(meth)acrylates described in EP 1 237 525 B1 usually have high levels of viscosities of significantly more than 1000 mPa·s and for this reason they lead to a low attainable fill level when the filler combination is unchanged, because the viscosities of the dental material may not increase overall so that the ability for further processing is not made worse. For this reason, the curable materials disclosed in this publication are still in need of improvement.

So that harmfulness to health due to Bisphenol A can be precluded and the impact strength of the materials improved, it would be desirable to waive Bisphenol A-containing monomers completely and to provide an alternative that makes the production of highly esthetic and high-strength dental material possible in a cost-effective way.

In EP 2 016 931 A2 and US 2009/003 565 A1, cycloaliphatic monomers on tricyclodecane derivatives (TCD) are cited in combination with dental glasses and conventional fillers such as quartz, glass ceramics and X-ray-opaque fillers (such as the trifluorides of the elements 52 through 71 described in DE 3 502 594 A1, in particular, ytterbium fluoride). Claimed are TCD-di-HEMA and DiHEA monomers in combination with Bisphenol-A-containing Bis-GMA monomers and dental glasses. A combination that is BPA-free without dental glasses based on fused silica and/or cristobalite is not disclosed. Further, no X-ray-opaque $YbF_3$ with a $SiO_2$ shell is disclosed unsilanized or silanized. The same applies to EP 1 719 497. Even though it discloses the complete substitution of Bis-GMA, neither the patent claims nor the example disclose a combination of (cyclo)aliphatic monomers (TCD derivatives) with fused silica and/or cristobalite.

EP 1 935 393 A2 discloses a dental composite consisting of acrylate monomers with a TCD (tricyclo[5.2.02.06]decane derivative) urethane structure. Neither the examples nor the patent claims describe a combination consisting of (cyclo)aliphatic meth(acrylate)-containing monomers with fused silica and/or cristobalite.

Specifically, the use of X-ray-opaque dental glasses is also combined with high costs, whereby the price is very highly dependent on the purity and the granularity. The average grain size $d_{50}$ of fillers is, however, a decisive criterion for the surface quality of the cured dental material. To be able to achieve a glossy surface without an additional finishing step, the average grain size should be smaller than 1 µm. Although such finely ground dental glasses are commercially available, they are highly priced because of the high grinding overhead, so that their use in temporary crowns or bridge materials is economically disadvantageous. For this reason, in modern provisional crowns and bridge materials that are intended to exhibit high gloss even without a separate finishing step in dental practice, aggregated or clustered amorphous nanoparticles are used as filler, which are significantly more economical than X-ray-opaque dental glasses. A significant disadvantage of such aggregated nanoparticles is associated, however, with a relatively high BET surface area, as a result of which the achievable fill level is significantly reduced. This results in the disadvantages that have already been cited above, such as a lower mechanical stability, a larger shrinkage of volume and an increased release of heat during the setting reaction.

In the case of core buildup materials and cements, a smooth surface is not very important, as these materials are usually covered by other materials. For this reason, here, most often relatively coarse-grained dental glasses are used that have a particle size up to 40 µm or in some cases even above that. Instead, the X-ray-opacity is in the foreground here as a further important criterion. It is important so that in an X-ray, the restoration material used can be distinguished from the natural tooth substance and that gaps that have formed between the natural tooth substance and the restoration can be identified.

DE 199 04 816 A1 discloses cold-polymerizing dental materials with initiator systems based on peroxide/amine or peroxide/barbituric acid. As additional customary accelerators, oxidizing substances are cited such as hydrogen peroxide, perester or inorganic oxidants. In the enumeration of fillers for dental materials that is not specified in further detail, the following are listed: glass and quartz powder, pyrogenic highly dispersed silicon dioxides as well as mixtures of these components. Even cristobalite, calcium silicate, zirconium silicate, bentonite and zeolite are mentioned, among others. Neither the examples nor the claims mention a specifically selected combination consisting of (cyclo)aliphatic monomers without Bisphenol-A-containing (meth)acrylate monomers.

DE 10 2010 046 697 A1 discloses polymerizable dental materials with a reactive paste-forming agent and in its description, even aliphatic and cycloaliphatic (meth)acrylate-containing monomers (such as, for example, also described in DE 2 816 823 C2) and in addition to other ingredients different fillers are also cited including—also not specified further—quartz, cristobalite and fused silica (page 14 [0091]. Neither the examples nor the claims disclose a specifically selected combination consisting of (cyclo)aliphatic monomers without Bisphenol-A-containing (meth)acrylate monomers and fused silica and/or cristobalite.

EP 1 790 323 A1 and/or U.S. Pat. No. 7,820,733 B2 describe two-component dual-hardening core buildup materials that have a lower viscosity and thus a better miscibility and achieve lower levels of discharge forces with static mixers in which specific selections of filler particle sizes are combined in pastes A and B. The specification, the patent examples or the claims do not disclose any BPA-free formulations in combination with fused silica and cristobalite.

A further example for a core buildup material that differentiates itself by the combination of fillers with specific particle sizes and by being drillable like human dentine is described in EP 2 237 763 B1.

Compared to known dental materials with comparable viscosity and flow properties, an increased filling degree is intended to be achieved by adding mono-dispersed, non-agglomerated organic polysiloxane particles, (Schmidt, H., et. al.: Institute for New Materials, Saarbrücken, in: Principles of the Production and Application of Sol-Gel Materials, handouts for the seminar on Sep. 19, 1994, page 1-46). Corresponding dental composites are disclosed in WO 01 30305 A1 and DE 196 17 931 A1. For use in provisional crowns and bridges, these formulations based on nanoparticles are, however, not economical because of the high price.

Curable dental masses containing fine X-ray-opaque amorphous inorganic materials and (meth)acrylic acid ester monomers without aromatic groups have also already been described. DE 199 01 783 A1 discloses dental restoration materials that have such a composition.

It is the objective of the present invention to provide an economical, preferably non-X-ray-opaque and BPA-free radically polymerizable dental material that can be processed as highly esthetic, provisional or definitive crown and bridge material in a dental practice into hardened shapes with excellent mechanical properties, in particular, a high impact strength and optimal surface properties without a separate finishing step. A further objective consists therein, to provide X-ray-opaque and preferably BPA-free esthetic materials that are suitable for use as core buildup material having an excellent impact strength, and in a further embodiment, can also be used as esthetic cement. In a preferred embodiment, a curable dental material is provided that has excellent storage stability and reproducible curing times under conditions in the mouth. In a further embodiment, such a material can also be used as block and disc material for millable CAD-CAM restorations.

The subject matter of the present invention is a radically polymerizable dental material containing:
  a) at least one curable aliphatic and/or cycloaliphatic monomer system with a refractive index as measured at 23° C. and a wave length of 589 nm that is smaller or equal to 1.50, that contains at least one aliphatic and/or cycloaliphatic bis(meth)acrylate and/or at least one aliphatic and/or cycloaliphatic bis(meth)acrylamide, and in particular, contains urethane group-containing (meth) acrylate monomers in the monomer mixture of ≥50% by weight, preferably ≥60% by weight, in particular, ≥70% by weight, relative to the monomer mixture respectively, and optionally with an impact-strength-modifying (meth)acrylate monomer that is ≤20% by weight, in particular, 1-20% by weight, relative to the monomer mixture and, in particular, with a preferred resistance to impact of the cured product of ≥55 MPa. and
  b) 15 to 80% by weight, advantageously 20 to 80% by weight, particularly preferred, 35 to 75% by weight, particularly preferred 40 to 70% by weight relative to the total mass of the dental material, at least one filler selected from the group of fused silica having a refractive index measured at 23° C. and a wave length of 589 nm of 1.45 to 1.47, advantageously 1.455 to 1.465 (approx. 1.46) or cristobalite with a refractive index measured at 23° C. and a wavelength of 589 nm of 1.48 to 1.49, advantageously, 1.484 to 1.487 or their combinations.

The curable dental materials according to the invention can be processed into highly esthetic, provisional or definitive crown and bridge materials or into core buildup materials as explained above. In the former case, component b) will more likely be selected from the fine-particulate range of grain sizes while in the latter case, component b) is more likely selected from the coarser size range of particles and additionally, an X-ray-opaque filler must be present as component c).

In a first embodiment, the invention preferably relates to a radically polymerizable dental material containing the ingredients a) and b) as defined above in the aforementioned amounts, whereby the average grain size $d_{50}$ as determined by sedimentation analysis of filler b) or fillers b) is between 0.2 and 1.0 µm. Preferably, the BET surface area of filler b) or fillers b) is between 10 and 20 $m^2/g$ in this embodiment. Preferably, the first embodiment of the dental material does not contain any X-ray-opaque fillers.

In a second embodiment, the invention preferably relates to a radically polymerizable dental material containing ingredients a) and b) as defined above in the indicated amounts, whereby the average grain size $d_{50}$ of filler b) or the fillers b) that was determined with a laser diffraction particle size measuring device, the Malvern Mastersizer 3000 with Hydro MV dispersion unit, is between 1.0 and 50 µm, advantageously between 1.0 and 20 µm, and preferably, the BET surface area of filler b) or fillers b) is between 2 and 6 $m^2/g$ in this embodiment, and 5 to 50% by weight, preferably 10 to 30% by weight, and particularly preferred 15 to 25% by weight relative to the total mass of the dental material, an X-ray-opaque filler c), that contains an irregularly shaped or spherical $YbF_3$— or $YF_3$— powder with an average grain size of the primary particles of 40 nm to 1.5 µm, and particularly preferred, a core/shell combination product consisting of $YF_3$— or $YbF_3$— core and $SiO_2$ shell, whereby particularly preferred, the $SiO_2$ shell surface is silanized. In particular, such a core/shell combination product consisting of $YF_3$— or $YbF_3$— core and $SiO_2$ shell has a refractive index of 1.48 to 1.54, an average grain size—measured with a laser diffraction particle size measurement device SALD 2001 (Schimadzu)—of the agglomerated particles between 0.5 and 5 µm, and a BET surface area, measured with a Tristar 3000 device from Micromeritics of 2 to 5 $m^2/g$.

Ingredient a) can be any aliphatic and or cycloaliphatic compound containing at least one acrylic acid ester and/or methacrylic acid ester residues or aliphatic or cycloaliphatic compounds including at least one acrylic acid amide and/or methacrylic acid amide residues. In the following, acrylic acid residues and/or methacrylic acid residues are also referred to as (meth)acrylic acid residues. In addition to monomeric compounds, oligomeric and polymeric (meth) acrylates or (meth)acrylamides are also suitable provided they still have polymerizable (meth)acrylate groups. Ingredient a) is selected in such a way that it has a refractive index measured at 23° C. and at a wave length of 589 nm (of the sodium D line), that is smaller than or equal to 1.50. The individual compound or the mixture of compounds forming ingredient a) differentiate themselves by the absence of aromatic groups such as phenyl, phenylene or Bisphenol A residues, i.e. they have this comparably low refractive index.

Preferably, ingredient a) is an aliphatic and/or cycloaliphatic system that contains two or more (meth)acrylate groups, in particular, diesters with acrylic acid and/or methacrylic acid. Within the scope of this specification, (meth)acrylate is a methacrylate, an acrylate or a mixture of methacrylates and acrylates. This correspondingly applies to the term (meth)acrylamide.

Preferably, ingredients a) are mixtures consisting of monofunctional and multifunctional acrylates and/or methacrylates represented by Formula VII

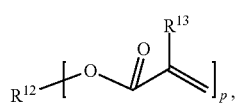

(VII)

wherein $R^{12}$ is a p-valent aliphatic and/or cycloaliphatic residue that may comprise one or several substituents, and that may comprise one or several ether oxygen atoms, and wherein $R^{13}$ means hydrogen or methyl, and p is a whole number from 1 to 12.

Examples of the preferably used (meth)acrylate compounds are at least bifunctional acrylic acid and/or (meth)acrylic acid esters. Thereby, these can be monomeric or polymeric acrylates and methacrylates. These differentiate themselves by the absence of aromatic groups such as phenyl, phenylene or Bisphenol A residues.

Well suited are, for example, acrylic acid and methacrylic acid diesters or higher esters, at least bifunctional aliphatic alcohols, oligomeric or polymeric ether and (meth)acrylates with one or more urethane bonds.

The aliphatic alcohols can be, for example, alpha, omega substituted alkanes such as ethylene glycol, propylene glycol, 1,4-butanediol, 1,6 hexanediol, 1,10-decanediol, 1,12-dodecanediol or further alcohols in this series. Likewise suitable are alcohols with secondary OH groups such as, for example, 1,3 butanediol or alcohols with cyclic structures such as, for example, tricyclo[$5.2.1.0^{2.6}$]decane.

Examples for esters of (meth)acrylic acid with oligomeric or polymeric ethers are triethylene glycol di(meth)acrylate, tetraethylene glycol (meth)acrylate, polyethylene glycol di(meth)acrylate, polypropylene glycol di(meth)acrylate and/or polybutylene glycol di(meth)acrylate, in particular, polytetramethylene glycol di(meth)acrylate.

Also well suited are the diacrylic and dimethacrylic acid esters of bis(hydroxymethyl)-tricyclo[$5.2.1.0^{2.6}$]decane and the diacrylic and di(meth)acrylic acid esters of compounds of bis(hydroxymethyl) tricyclo[$5.2.1.0^{2.5}$]decane extended with compounds of 1 to 3 ethylene oxide and/or propylene oxide units as cited in DE 28 16 823 C2.

Examples for higher esters of (meth)acrylic acid are trimethylolpropane tri(meth)acrylate and pentaerythritol tri(meth)acrylate.

Examples for (meth)acrylate with urethane bond(s) are di-2-(meth)acryloxyethyl-2,2',4-trimethylhexamethylene dicarbamate, di-2-(meth)acryloxyethyl-2,4,4'-trimethylhexamethylene dicarbamate and 1,3,5-tris[1,3-bis{(meth)acryloyloxy}-2-propoxycarbonyl aminohexane]-1,3,5-(1H,3H,5H)triazin-2,4,6-trion. In addition, this can also be a (meth)acrylate of a urethane oligomer that is derived from 2,2'-di(4-hydroxycyclohexyl)propane, 2-oxepanon, hexamethylene diisocyanate and 2-hydroxyethyl(meth)acrylate, and a (meth)acrylate of a urethane oligomer, that is derived from 1,3-butanediol, hexamethylene diisocyanate and 2-hydroxyethyl (meth)acrylate. These (meth)acrylates can be used by themselves or as a mixture of two or more.

Furthermore, well suited monomers are the (meth)acrylic acid esters described in EP 0 235 826 A1, for example, triglycolic acid bis[3(4)-(meth)acryloxymethyl-8(9)-tricyclo[$5.2.1.0^{2.6}$]decylmethyl ester].

Of course, mixtures consisting of monomers and/or unsaturated polymers produced therefrom can also be used as component a).

Particularly preferred are mixtures consisting of aliphatic and/or cycloaliphatic bis(meth)acrylates and/or aliphatic and/or cycloaliphatic bis(meth)acrylamides in which at least one of the mixing partners has one or several urethane groups and in which at least one of the mixing partners does not have a urethane group.

Particularly preferred is the use of mixtures of aliphatic and/or cycloaliphatic bis(meth)acrylates in which at least one of the monomers has one or more urethane groups, and in which at least one of the monomers does not have a urethane group.

These preferably used mixtures can also contain further radically polymerizable (meth)acrylates, preferably those without aromatic groups and, in particular, groups that are not derived from Bisphenol A.

Cured products consisting of mixtures of monomers with and without urethane groups differentiate themselves by having very good mechanical properties such as high moduli of elasticity and high flexural strengths.

In a further embodiment, at least bifunctional acrylic acid and methacrylic acid esters up to 20% relative to ingredient a), preferably up to 10% mono-functional (meth)acrylic acid esters such as methyl(meth)acrylate can also be used.

Further preferred examples of (meth)acrylates include: Methyl(meth)acrylate, ethyl(meth)acrylate, isopropyl(meth)acrylate, n-butyl(meth)acrylate, isobutyl(meth)acrylate, tetrahydro-furfuryl(meth)acrylate, glycidyl(meth)acrylate, 2-methoxyethyl-(meth)acrylate, 2-ethoxyethyl(meth)acrylate, 2-methoxyethyl(meth)acrylate, 2-ethylhexyl(meth)acrylate, 2-hydroxy-1,3-di(meth)acryloxy propane, 2-hydroxyethyl(meth)acrylate, hydroxypropyl(meth)acrylate; neopentyl glycol di(meth)acrylate, 1,14-tetra-decanediol di(meth)acrylate, 1,16-hexadecanediol di(meth)acrylate, trimethylolethane tri(meth)acrylate, dipentaerythritol penta(meth)acrylate, dipentaerythritol hexa(meth)acrylate, trimethylolmethane tri(meth)acrylate, pentaerythritol tetra(meth)acrylate, mono or polyethylene glycol di(meth)acrylate, e.g. ethylene glycol di(meth)acrylate, diethylene glycol di(meth)acrylate and triethylene glycol di(meth)acrylate, and mono or propylene glycol di(meth)acrylate, whereby the polyalkylene glycol derivatives include those with branched as well as with linear structures.

Particularly well suited for dissolving, for example, barbituric acid derivatives or malonyl sulfamides and organic halides, are ingredients a) that contain tetrahydrofurfuryl (meth)acrylate, glycidyl(meth)acrylate, 2-hydroxyethyl (meth)acrylate, 2-hydroxypropyl(meth)acrylate, 3-hydroxypropyl(meth)acrylate and 2-hydroxy 1,3-di(meth)acrylate.

Some of the aliphatic and/or cycloaliphatic bis(meth)acrylates and/or aliphatic and/or cycloaliphatic bis(meth)acrylamides cited as component a) give the cured product an improved impact strength. As a rule, these are low viscous types having a viscosity of less than 2000 mPa·s, preferably less than 1000 mPa·s, particularly preferred, less than 500 mPa·s, as measured at a temperature of 23° C. with a cone/plate geometry of (35 mm, 4°), and a shear stress of 50 Pa.

Particularly preferred components a) that are used as impact strength modifiers are low viscous (meth)acrylates and bis(meth)acrylates that are free of aromatic compounds, urethane groups and urea groups and have a viscosity of less than 2000 mPa·s, preferably less than 1000 mPa·s, particularly preferred less than 500 mPa·s, as measured at a temperature of 23° C. with a cone/plate geometry (35 mm, 4°) and a shear stress of 50 Pa.

Additional particularly preferred impact strength modifiers are polytetramethylene glycol di(meth)acrylate, in particular, the types with an average mole mass of 5,000 g/mol to 300 g/mol, for example, from approx. 4,600 g/mol, 3,000 g/mol, 2,100 g/mol, 1,900 g/mol, [1,900 g/mol], 1,500 g/mol, 1,100 g/mol, 750 g/mol or 350 g/mol. Particularly preferred are polytetramethylene glycol di(meth)acrylates with an average molecular weight of 1,500 g/mol to 300 g/mol, for example, from approx. 1,500 g/mol, 1,100 g/mol, 750 g/mol or 350 g/mol, and, in particular, from 1,000 g/mol to 300 g/mol, that have a viscosity of less than 2000 mPa·s, preferably less than 1000 mPa·s, particularly preferred, less than 500 mPa·s as measured at a temperature of 23° C. with a cone/plate geometry (35 mm, 4°) and a shear stress of 50 Pa.

These impact strength modifiers are generally used in combination with other compounds of component a). The impact strength modifier that is preferably used is polytetramethylene glycol di(meth)acrylate.

Particularly preferred, the impact strength modifiers are used in combination with mixtures of aliphatic and/or cycloaliphatic bis(meth)acrylates in which at least one of the mixing partners has one or more urethane groups and in which at least one of the mixing partners does not have a urethane group. As component a), preferred dental masses according to the invention contain a mixture of aliphatic and/or cycloaliphatic bis(meth)acrylates and if appropriate, aliphatic and/or cycloaliphatic mono-functional (meth) acrylic acid esters, whereby component a) contains 1 to 20% by weight relative to the total amount of component a) of polytetramethylene glycol di(meth)acrylate(s), and whereby the mixture has a refractive index as measured at 23° C. and at a wavelength of 589 nm that is smaller than or equal to 1.50.

The curable aliphatic and/or cycloaliphatic monomer system of component a) must have a refractive index that is smaller than or equal to 1.50. Thereby, individual components of this curable system can also have a refractive index that is more than 1.5 as long as the complete curable system meets the requirement of having a refractive index that is smaller than or equal to 1.50.

Preferably all radically polymerizable components of the dental mass according to the invention are selected in such a way that the mixture of these components has a refractive index as measured at 23° C. and at a wavelength of 589 nm that is smaller than or equal to 1.50.

Particularly preferred ingredients of component a) and preferred curable aliphatic and/or cycloaliphatic systems of component a) have a refractive index, as measured at 23° C. and at a wavelength of 589 nm, of 1.46 to 1.49.

If other ingredients of alkyl residues are cited in the compounds of ingredient a) or in the chemical compounds listed in the following, these are saturated or branched or unbranched aliphatic hydrocarbon residues. As a rule, the length of their chain is up to 12 C atoms. $C_1$ to $C_8$ alkyl residues are preferred. Examples of this are methyl, ethyl, n-propyl, isopropyl, n-butyl, sec.-butyl, tert.-butyl, n-pentyl, n-hexyl or 2 ethylhexyl. Alkyl residues can be substituted where appropriate, for example, with one or more alkoxy, amino or hydroxy residues or with acidic residues such as, for example, with phosphoric acid groups, phosphonic acid groups, sulfonic acid groups and/or carboxylic acid groups as well as their anhydrides, or with one or more halogen atoms, for example, chlorine atoms, or with a combination of two or more of these substituents.

If cycloalkyl residues are cited in the compounds of ingredient a) or in the chemical compounds of other ingredients listed in the following, these are saturated cycloaliphatic hydrocarbon residues. As a rule, these have five to eight carbon ring atoms.

Preferred are cyclopentyl, or particularly, cyclohexyl residues. These residues can have one or several cycloalkyl rings. Several cycloalkyl rings can be linked with each other by covalent bonds or bridge groups or form bicyclic or polycyclic ring systems, for example, tricyclo [$5.2.1.0^{2.6}$]decane. If appropriate, the cycloalkyl residues can be substituted, for example, with one or several alkyl, alkoxy, amino or hydroxy residues or with acidic residues such as, for example, with phosphoric acid groups, phosphonic acid groups, sulfonic acid groups and/or carboxylic acid groups, as well as their anhydrides, or with one or more halogen atoms, for example, chlorine atoms or with a combination of one or several of these substituents.

If alkylene glycol ether residues are cited in the compounds of ingredient a) or in the chemical compounds of other ingredients listed in the following, these are residues derived from saturated branched or unbranched aliphatic alkylene glycols. These residues can have one or several repeating structural units. As a rule, the alkyl units have two to four carbon atoms. Examples for residues of this type are $—[C_2H_4—O]_q—$, $—[C_3H_6—O]_q—$ and $—[C_4H_8—O]_q—$, where q=1-30. Alkylene glycol ether residues can likewise be substituted, for example, with one or several alkoxy, amino or hydroxy residues or with one or several halogen atoms, for example, chlorine atoms or with a combination of two or more of these substituents.

As filler b) fused silica and/or cristobalite is present in the curable composites according to the invention having the selected refractive index as described above; for fused silica: 1.45 to 1.47 preferably 1.455 to 1.465, in particular, 1.46 and/or for cristobalite: 1.48 to 1.49 preferably 1.484 to 1.487, in particular, 1.485.

Particularly preferred is the use of cristobalite or mixtures of fused silica and cristobalite.

The substances used as fillers b) in a first embodiment according to the invention are very fine-particulate products. As a rule, these are produced by grinding fused silica or cristobalite. Particularly preferred are so-called ultra-fine powders. These are products having grains that are primarily in the submicron range.

Fused silica is an amorphous silicon dioxide that may contain small amounts of contaminations (e.g. in the weight range of 1,000 ppm). These can be soda oxide or calcium oxide contaminations. The fused silica can be of natural origins or artificially produced, e.g. by melting and once again solidifying quartz.

Cristobalite is a naturally occurring mineral and is a high temperature modification of silicon dioxide. Cristobalite occurs in an alpha form and a beta form. Both variants can be used as ingredient b) according to the invention.

The product or product mixture used as ingredient b) according to the invention differentiates itself by a refractive index as measured at 23° C. and at a wavelength of 589 nm that is between 1.45 and 1.49. The refractive index of cristobalite is thereby in the range of 1.48 to 1.49 and the refractive index of the fused silica used according to the invention is 1.45 to 1.47, preferably approx. 1.46.

Ingredients b) used in the first embodiment according to the invention differentiate themselves by a high degree of fineness of the grain size. The diameter of the predominant share of the particles of these ingredients is in the submicron range.

Within the scope of this specification, the particle diameter of the fine-grained ingredients b) is determined by sedimentation analysis. In this process, a Sedigraph® 5100 from Micromeritics Instrument Corporation, Norcross, Ga., USA is used. The results of the sedimentation analysis are obtained in the form of a velocity-of-descent-equivalent diameter, whereby a spherical shape of the particles is assumed. In the sedimentation analysis, the volume or the weight percentage of the particles can be determined within a predetermined diameter range. For the purposes of this specification, volume percentages are used. The coarse particles descend fastest during the sedimentation analysis. As a result, the dispersion of the particle sizes can be determined as well as an average particle size. The upper limit of the particle diameter for the range from 0 to 10% by volume of the sedimented particles in the sedimentation analysis is referred to as $d_{10}$. The upper limit of the particle diameter for the range of 0 to 50% by volume of the sedimented particles in the sedimentation analysis is referred to as $d_{50}$. The upper limit of the particle diameter for the range of 0 to 90% by volume of the sedimented particles of the sedimentation analysis is referred to as $d_{90}$. Within the scope of this specification, the average particle size is the value $d_{50}$, which is determined by sedimentation analysis with the Sedigraph® 5100.

The fine-grained products of ingredient b) are, inter alia, identified thereby that their average grain size, expressed as $d_{50}$ values, ranges between 0.2 and 1.0 µm, preferably between 0.3 and 0.8 µm.

Preferred fine-grained products of ingredient b) have a distribution of the particle diameters in which
the volume percentage of the particles with a diameter of 2 µm is less than 1%, preferably 0%
the volume percentage of the particles with a diameter between 2 and 1 µm is less than 10%, preferably 0 to 5%,
the volume percentage of the particles with a diameter between 1 and 0.6 µm is more than 10%, preferably 15 to 40%,
the volume percentage of the particles with a diameter between 0.6 and 0.3 µm is more than 20%, preferably 25 to 50%,
the volume percentage of the particles with a diameter of less than 0.3 µm is more than 10%, preferably 10 to 20%.

Such fine-grained fillers preferably have a BET surface area between 10 and 20 $m^2/g$.

The ingredients b) used in the second embodiment according to the invention differentiate themselves by having larger granulations. The diameter of the preponderant share of the particles of these ingredients is in the micron range.

Within the scope of this specification, the particle diameter of the coarser ingredients b) is determined with a laser diffraction particle size measurement device, the Malvern Mastersizer 3000 with Hydro MV dispersing unit. The coarser ingredients b) have a particle diameter between 1 and 50 µm, preferably 1 to 20 µm.

Preferred products of the coarser ingredient b) have a distribution of the particle diameters in which
the volume percentage of the particles with a diameter of more than 20 µm is less than 10%, preferably 0%
the volume percentage of the particles with a diameter larger than 15 µm is 0 to 20%, preferably 0 to 10%,
the volume percentage of the particles with a diameter larger than 10 µm is 10 to 40%, preferably 20 to 30%,
the volume percentage of the particles with a diameter larger than 5 µm is 40 to 80%, preferably 50 to 70%,
the volume percentage of the particles with a diameter larger than 2 µm is 70 to 100%, preferably 80 to 100%,
the volume percentage of the particles with a diameter larger than 1 µm is 80 to 100%, preferably 90 to 100%.
the volume percentage of the particles with a diameter larger than 0.5 µm is 90 to 100%, preferably more than 95%.

Such fillers preferably have a BET surface area between 2 and 6 $m^2/g$.

Ingredients b) used according to the invention can be fused silica by itself, cristobalite by itself or preferably combinations of fused silica and cristobalite. The weight ratio of fused silica to cristobalite is typically 1:1 to 10, in particular, 1:2 to 5, particularly preferred 1:2 to 4 and particularly preferred, 1:2, 5.

Ingredient b) is used having a level of purity of at least 95% relative to the unsilanized filler. Preferably, non-X-ray-opaque types are used, in particular, those types having a degree of purity that is at least 98% (determined by chemical analysis of the unsilanized filler).

Fillers b) used according to the invention typically have traces of contaminations, whereby these contain the following: $Al_2O_3 \leq 0.3\%$, $Fe_2O_3 \leq 0.05\%$, $CaO+MgO \leq 0.4\%$, $Na_2O+K_2O \leq 0.3\%$ and $ZrO_2 \leq 0.5\%$. This information relates to the weight of the contamination respectively.

These fillers b) and the, optionally additionally present non-X-ray-opaque fillers are selected in such a way that they can be formulated as radically polymerizable dental material having an X-ray visibility determined according to DIN EN ISO 4049 of less than 1 mm (aluminum equivalent).

In a second embodiment of the dental material according to the invention, larger amounts of the selected X-ray-opaque fillers are present. These are irregularly shaped or spherical $YbF_3$— or $YF_3$— powders with an average grain size of the primary particles of 40 nm to 1.5 µm, and particularly preferred, core/shell combination products consisting of $YF_3$— or $YbF_3$— core and $SiO_2$ shell, whereby very specially preferred, the $SiO_2$ shell surface is silanized. In particular, such a core and shell combination product has a refractive index of 1.48 to 1.54, an average particle size as measured with a laser diffraction particle size measurement device, the SALD-2001 (Schimadzu), of the agglomerated particles between 0.5 and 5 µm, and a BET surface area as measured with a Tristar 3000 device from Micromeritics of 2 to 5 $m^2/g$. Thereby, the refractive index of the core/shell combination product consisting of $YbF_3$— core and $SiO_2$ shell, is between 1.52 and 1.54.

Ingredients b) as well as the optionally present further fillers can optionally also be hydrophobic as the result of treatment with silanes. Particularly suited for this are, for example, 3-methacryloxypropyltrimethoxy silane or trimethyl silane.

In addition to ingredients b) and if appropriate c) the polymerizable dental material may comprise even further customary dental fillers with the exception of fused silica, cristobalite and X-ray-opaque fillers. Their selection is determined thereby, that the cured mold must have sufficient translucency or a sufficient X-ray-opaqueness.

These additional fillers are inorganic or organic materials. Examples of inorganic materials are silicon dioxide in its various modifications with the exception of fused silica and cristobalite (such as, for example, quartz, feldspar), ground glass, alumina glass, kalium glass and fluoroaluminosilicate glass, as well as hardly soluble fluorides such as $CaF_2$, also silica gels as well as silicon dioxide, in particular, pyrogenic silicon dioxide or its granulates, or synthetic zeolite, calcium phosphate, aluminum silicate, calcium silicate, magnesium carbonate, hydrated calcium silicate or hydrated aluminum silicate (Kaolin).

These fillers can be subjected to a surface treatment, for example, with γ-(meth)acryloxypropyl-trimethoxysilane, vinyltrichlorosilane, vinyltriethoxysilane, vinyltrimethoxysilane, vinyltriacetoxysilane, vinyltri(methoxyethoxy)silane, alkyltrichlorosilane, alkyltriethoxysilane, alkyltrimethoxysilane, alkyltriacetoxysilane, alkyltri (methoxyethoxy)-silane, in particular, methyltrichlorosilane, methyltriethoxysilane, methyltrimethoxysilane, methyltriacetoxysilane and methyltri(methoxyethoxy)silane, in particular, 3(meth)acryloxypropyl-trimethoxysilane, 3-(meth)acryloxypropyl-triethoxysilane.

Furthermore, usable organic-inorganic composite fillers can be produced by mixing the aforementioned fillers with a polymerizable monomer or oligomer, hardening the mixture and subsequently pulverizing the cured mixture. Also suitable are polymethyl(meth)acrylate pearls or other pulverized organic polymerizates that are already completely pigmented. To increase the flexibility of the dental masses it can also be advantageous to use soluble organic polymers. Suitable are, for example, polyvinyl acetate and co-polymers based on vinyl chloride/vinyl acetate, vinyl chloride/vinyl isobutyl ether and vinyl acetate/maleic acid dibutyl ether.

Advantageously, as additional optional fillers, even nanoparticulates, clusters, aggregates and agglomerates such as fillers with a BET surface area larger than 30 $m^2/g$, preferably 30 to 400 $m^2/g$, particularly preferred of 30 to 250 $m^2/g$ are used. Their percentage relative to the total mass of the polymerizable dental material is customarily up to 15% by weight, preferably 0.1 to 10% by weight. Within the scope of this specification, nanoparticulate fillers refer to those fillers that have primary particles of a size that is smaller than 100 nm. Examples of this are pyrogenic silicon dioxides (HDK/Wacker/Aerosil/Evonik) or precipitated silicon dioxides (Sipernat/Evonik).

Preferred are radically polymerizable dental masses containing the components a) and b) as defined above and if appropriate, c) and d) 0.1 to 15% by weight relative to the dental mass of nanoparticulate fillers with a BET surface area of 30 to 400 $m^2/g$.

For dyeing the cured mold, the radically polymerizable dental material preferably also has, in addition to ingredients a), b) and if appropriate c), a white, black, red and/or yellow organic or, in particular, inorganic pigment. The type and amount of these pigments is selected by the person skilled in the art in order to achieve a shade of color that corresponds to the natural color of the teeth. The person skilled in the art is familiar with this procedure.

The radically polymerizable dental material according to the invention further contains at least one initiator of the radical polymerization e). Different systems can be formulated. Examples of this are radiation-curable dental masses that have at least one photoinitiator; or chemically hardening dental masses that have at least one redox initiator; or dual-hardening dental masses that have a combination of photo-initiator and redox initiator; or thermally hardening dental masses that have radical starters that can be thermally activated, for example, peroxides, hydroperoxides or azo compounds. The person skilled in the art is familiar with these types of initiator classes.

The radically polymerizable dental material according to the invention is preferably provided in a form that allows for adequate storage.

Typically, the radically polymerizable dental material according to the invention is provided in the form of multi-component systems, in particular, of chemically or dually hardening two-component systems. Thereby, the individual ingredients of the individual components are selected in such a way that their combination results in a mixture that can be stored. On the other hand, by mixing these two individual components, the polymerizable the dental material is produced that quickly hardens under the conditions in the mouth (temperature and humidity).

The storage form of the individual components can differ. Liquid-paste systems are typical or, in particular, paste-paste systems.

Preferred is a radically polymerizable dental material in the form of a pasty two-component system consisting of a base paste A and of initiator paste B, whereby the base paste A has the following components:

19 to 80% by weight relative to the total mass of component A of a mixture of mono and multifunctional acrylates and/or methacrylates a), that have a refractive index at 23° C. and a wavelength of 589 nm between 1.46 and 1.50, 19 to 80% by weight relative to the total mas of component A of a cristobalite and/or fused silica b) that preferably has an average grain size $d_{50}$ of 0.3 to 0.8 μm, and preferably a specific surface area of 10 to 20 $m^2/g$ that was determined according to the BET method, whereby the cristobalite has a refractive index at 23° C. and at a wavelength of 589 nm of 1.484 to 1.487 and the fused silica has a refractive index at 23° C. and a wavelength of 589 nm of 1.455 to 1.465, 1 to 15% by weight relative to the total mass of component A of a pyrogenic silicon dioxide d) with a specific surface of 30 to 400 $m^2/g$ that was determined according to the BET method, at least one metal compound f), at least one halogenide and/or pseudohalogenide compound g), and optionally, one or several photo inhibitors and/or photo co-initiators e)

whereby the initiator paste B has the following components:

19 to 80% by weight relative to the total mass of component B of a paste-forming agent j), in particular, a paste-forming agent j) that has a refractive index at 23° C. and a wavelength of 589 nm between 1.460 and 1.520, 0 to 80% by weight relative to the total mass of component B of a cristobalite and/or fused silica b), that preferably has an average grain size $d_{50}$ of 0.3 to 0.8 μm, and preferably, a specific surface area of 10 to 20 $m^2/g$ that was determined according to the BET method, whereby the fused silica has a refractive index at 23° C. and a wavelength of 589 nm of 1.455 to 1.465, and whereby the cristobalite has a refractive index at 23° C. and a wavelength of 589 nm of 1.484 to 1.487, 0 to 80% by weight of other customary dental fillers with the exception of fused silica and cristobalite, 1 to 15% by weight relative to the total mass of component B of a barbituric acid derivative and/or a malonyl sulfamide e), and 0 to 2% by weight preferably 0.1 to 1.5% by weight relative to the total mass of component B of an organic per compound h), in particular, an organic perester compound, and optionally, one or more photoinitiators and/or co-initiators e).

A particularly preferred form for storing polymerizable dental materials is disclosed in DE 10 2010 046 697 A1. These are paste-paste systems. Particularly advantageously, the polymerizable dental material according to the invention is used in the form of this system.

Furthermore, preferred is a radically polymerizable dental material in the form of a pasty two-component system consisting of base paste A and initiator paste B,
   whereby the base paste A has the following components:
   18.99 to 80% by weight relative to the total mass of component A of a mixture consisting of mono and multifunctional acrylates and/or methacrylates a), that have a refractive index at 23° C. and a wavelength of 589 nm between 1.46 and 1.50,
   18.99 to 80% by weight relative to the total mass of component A of a cristobalite and/or fused silica b), which preferably has an average grain size $d_{50}$ of 0.3 to 0.8 µm, and preferably a specific surface area of 10 to 20 $m^2/g$ that was determined according to the BET method, whereby the cristobalite has a refractive index at 23° C. and a wavelength of 589 nm of 1.484 to 1.487, and the fused silica has a refractive index at 23° C. and a wavelength of 589 nm of 1.455 to 1.465,
   1 to 15% by weight relative to the total mass of component A of a pyrogenic silicon dioxide d) with a specific surface area of 30 to 400 $m^2/g$ that was determined according to the BET method, and
   0.01 to 2% by weight relative to the total mass of component B of an amine, in particular, an aromatic amine, and optionally, one or more photo initiators and/or co-initiators e), and
   whereby the initiator paste B has the following components:
   19.99 to 80% by weight relative to the total mass of component B of a mixture consisting of mono and multifunctional acrylates and/or methacrylates a) that have a refractive index at 23° C. and a wavelength of 589 nm between 1.46 and 1.50,
   19.99 to 80% by weight relative to the total mass of component B of a cristobalite and/or fused silica b), which preferably has an average grain size $d_{50}$ of 0.3 to 0.8 µm, and preferably has a specific surface area of 10 to 20 $m^2/g$ that was determined according to the BET method, whereby the fused silica has a refractive index at 23° C. and a wavelength of 589 nm of 1.455 to 1.465, and whereby the cristobalite has a refractive index at 23° C. and a wavelength of 589 nm of 1.484 to 1.487,
   0.01 to 2% by weight relative to the total mass of component B of at least one organic peroxide h), and
   one or more photoinitiators and/or co-initiators e).

Further preferred is a radically polymerizable dental material in the form of a pasty two-component system consisting of a base paste A and an initiator paste B,
   whereby the base paste has the following components:
   13.99 to 80% by weight relative to the total mass of component A of a mixture consisting of mono and multifunctional acrylates and/or methacrylates a) that have a refractive index at 23° C. and a wavelength of 589 nm between 1.46 and 1.50,
   18.99 to 80% by weight relative to the total mass of component A of a cristobalite and/or fused silica b) which preferably has an average grain size $d_{50}$ of 0.8 to 20 µm, and preferably a specific surface area determined according to the BET method of 0.5 to 20 $m^2/g$, whereby the cristobalite has a refractive index at 23° C. and a wavelength of 589 nm of 1.484 to 1.487 and the fused silica has a refractive index at 23° C. and a wavelength of 589 nm of 1.455 to 1.465,
   5 to 30% by weight relative to the total mass of component A of X-ray-opaque additives c) whereby these are irregularly shaped or spherical $YbF_3$— or $YF_3$— powders having an average grain size of the primary particle of 40 nm to 1.5 µm, and particularly preferred, core/shell combination products consisting of $YF_3$— or $YbF_3$— core and $SiO_2$ shell, whereby, particularly preferred, the $SiO_2$ shell surface is silanized. In particular, such a core/shell combination product has a refractive index of 1.48 to 1.54, an average grain size of the agglomerated particles between 0.5 and 5 µm as measured by a laser refraction particle size measurement device, the SALD 2001 (Schimadzu), and a BET surface area measured with a Tristar 3000 device from Micromeretics, of 2 to 5 $m^2/g$.
   1 to 15% by weight relative to the total mass of component A of a silicon dioxide on the nanoscale and/or $SiO_2$ d) that is present in the form of primary particles, clusters, aggregates and/or agglomerates having a specific surface area as measured according to the BET method of 30 to 400 $m^2/g$, and
   0.01 to 2% by weight relative to the total mass of component A of an amine, in particular, an aromatic amine, and optionally, one or several photoinitiators and/or additional co-initiators e), and
   whereby the initiator paste B has the following components:
   13.99 to 80% by weight relative to the total mass of component B of a mixture consisting of mono and multifunctional acrylates and/or methacrylates a) having a refractive index at 23° C. and at a wavelength of 589 nm of between 1.46 and 1.50,
   18.99 to 80% by weight relative to the total mass of component A, of a cristobalite and/or fused silica b) that preferably have an average grain size $d_{50}$ of 0.8 to 20 µm, and preferably a specific surface area of 1.0 to 20 $m^2/g$ as determined by the BET method, whereby the cristobalite has a refractive index at 23° C. and a wavelength of 589 nm of 1.484 to 1.487 and the fused silica has a refractive index at 23° C. and a wavelength of 589 nm of 1.455 to 1.465.
   5 to 30% by weight relative to the total mass of component B of X-ray-opaque additives c) whereby these are irregularly shaped or spherical $YbF_3$— or $YF_3$— powders having an average granulate size of the primary particles of 40 nm to 1.5 µm, and particularly preferred, they are core/shell combination products consisting of $YF_3$— or $YbF_3$— core and $SiO_2$ shell, whereby particularly preferred, the $SiO_2$ shell surface is silanized. In particular, such a core/shell combination product has a refractive index of 1.48 to 1.54, an average grain size of the agglomerated particles between 0.5 and 5 µm as measured with a laser refraction particle size measurement device, the SALD 2001 (Schimadzu), and a BET surface area of 2 to 5 $m^2/g$ as measured with at Tristar 3000 device from Micromeritics.
   1-15% by weight relative to the total mass of component B of a silicon dioxide on the nanoscale and/or $SiO_2$ d) that are present in the form of primary particles, clusters, aggregates and/or agglomerations having a specific surface area of 30 to 400 $m^2/g$ as measured by using the BET method,
   0.01 to 2% by weight relative to the total mass of component B of at least one organic peroxide h) and
   one or more photoinitiators and/or co-initiators e).

As components of initiators e) of the radical polymerization, preferably, barbituric acid derivatives are used.

Within the scope of the present specification, barbituric acid derivatives refer to barbituric acid, thiobarbituric acid and, in particular, substituted barbituric acids and substituted thiobarbituric acids. Salts of barbituric acids and their derivatives as well as thiobarbituric acids and its derivatives are precluded. Instead of barbituric acid derivatives, malonyl sulfamides can also be used.

Examples of particularly advantageously used barbituric acid derivatives are:

1-benzyl-5-phenylbarbituric acid, 1-cyclohexyl-5-ethylbarbituric acid, 1,3-dimethyl-5-cyclopentylbarbituric acid, 1,3-dimethyl-5-cyclohexylbarbituric acid, 1,3-dimethyl-5-ethylbarbituric acid, 1,3-dimethyl-5-isobutylbarbituric acid, 1,3-dimethyl-5-n-butylbarbituric acid, 1,5-dimethylbarbituric acid, 5-n-butylbarbituric acid, 5-cyclohexylbarbituric acid, 5-ethylbarbituric acid, 5-isobutylbarbituric acid, 5-isoproypylbarbituric acid and 1,3,5-trimethylbarbituric acid. These barbituric acid derivatives can be used by themselves or as a mixture of two or more thereof.

The advantageously used initiator system based on barbituric acid derivatives and/or malonyl sulfamides can be complemented or replaced with additional initiator systems that trigger the radical polymerization of the monomers a). These can be, for example, additional known initiators or initiator components such as, for example, inorganic peroxides, hydroperoxides, peracids or redox initiators or redox initiator components and/or photoinitiators. As the result of the combination of chemical and photo-chemical initiation, dual-hardening dental masses according to the invention can be produced.

Particularly suited as inorganic peroxide are alkali or earth alkali peroxide sulfates, in particular, sodium or potassium peroxydisulfate. Particularly suitable as redox initiator components are alkali or earth alkali toluol sulfinate, in particular, sodium or potassium toluol sulfinate. Advantageously, the sodium peroxydisulfate can be formulated in component A and the sodium toluol sulfinate can be formulated, if appropriate, with basic additives, in component B. Correspondingly, alkali and earth alkali sulfites can also be used.

Suitable as photoinitiators are, for example, alpha-diketones such as camphor quinone in combination with secondary and tertiary amines or mono and bisacylphospine oxide such as 2,4,6-trimethylbenzoyldiphenylphosphine oxide and bis-(2,6-dichlorobenzoyl)-4-n-propylphenylphosphine oxide and benzaldehyde such as, for example, p-n-octylbenzoldeclyd. But other compounds of this type are also suitable such as they are described in EP 0 073 413 A2, EP 0 007 508 A2, EP 0 047 902 A2, EP 0 057 474 A2 and EP 0 184 095 A2.

As metal compounds f) in the polymerizable dental material, preferably, compounds are used that are selected from the group of metal salts and/or metal complexes, in particular, the salts of the metals of the third and fourth main group and of the first through the eights subgroups of the periodic table, including the particularly preferred salts and complexes of copper, iron, tin, chromium, manganese, cobalt, zinc, nickel, the rare earth metals and aluminum, very specially preferred is a copper compound, in particular, copper acetyl acetonate, copper methacrylate, copper acrylate, copper acetate, cooper oleate, copper ethyl hexanoate or copper cyclohexyl butyrate.

In the polymerized dental materials according to the invention, halogenides or pseudohalogenides g) are advantageously used at 25° C. as water-soluble salts, preferably, halogenides or pseudohalogenides with metal cations from metals in the first and the second main group of the periodic table having ammonium or phosphonium cations, in particular, those with organic residues including the hydrohalogenides of amines, particularly preferred, a chloride, bromide or iodine.

Examples of the preferred ingredients g) are organic halogenides such as benzyl-tributylammonium chloride, benzyldimethylcetylammonium chloride, benzyl-dimethylstearylammonium chloride, benzyltriethylammonium bromide, benzyl-trimethylammonium chloride, cetylalkonium chloride, cetylpyridinium bromide, cetylpyridinium chloride, cetyltriethylammonium bromide, mono to tetraallylalkylammonium chloride, mono to tetraallylalkylammonium bromide, in particular, diallyldimethylammonium chloride, dodecyldimethylammonium chloride, dilauryldimethylammonium chloride, lauryldimethylammonium chloride, tetra-n-butylammonium bromide, tetra-n-butyl-ammonium chloride, tetradecyltrimethylammonium bromide, tetraethylammonium bromide and trioctylmethylammonium chloride, the corresponding phosphonium compounds or hydrohalogenides of tertiary amines, in particular, hydrochlorides of tertiary amines.

The compounds of ingredient g) can be used by themselves or in a mixture of two or several thereof.

To obtain more monomers it is further advantageous when the polymerized dental material contains—in one of the components as ingredient h)—up to 5% by weight relative to the total mass of the component of an organic peroxide compound. Preferably, ingredient h) is a carboxylic acid peroxyester, carbon dioxide peroxyester, diacyl peroxide, perketal, peracetal, perether, hydrogen peroxide, peracid or a combination of two or more thereof. Thereof, in particular, carboxylic acid peroxyester, carbon dioxide peroxyester and perketals are preferred. Particularly preferred, tert-butylperoxy-3, 5,5-trimethyl-hexanoate, tert-butylperoxybenzoate, tert-butylperoxy-2-ethylhexyl carbonate or combinations of two or more thereof are used.

If the dental material according to the invention contains the organic peroxide h), a metal compound f), a halogenide or pseudohalogenide g) and an initiator e) (barbituric acid derivatives/malonyl sulfamide) it is particularly expedient that the organic peroxide h), the initiator e) and the combination of metal compound f) and the halogenides or pseudohalogenide g) are present in two spatially separate components. For example, the organic peroxide h), the reactive paste-forming agent, an initiator e) (barbituric acid derivatives/malonyl sulfamide) and fillers b) and/or c) can be kneaded into a paste. On the other hand, the polymerizable monomers a) can also be present together with a combination of metal compound f) and halogenide or pseudohalogenide g) and fillers b).

In place of the initiator components identified above or in addition to them, other initiators e) can also be in the pastes. Particularly well suited are photoinitiators, benzoin alkyl ethers or benzoin alkyl esters, benzyl monoketals, acyl pho[s]phine oxides or aliphatic and aromatic 1,2-diketo compounds, for example, camphor quinone initiators that can be activated at room temperature in combination with a co-initiator 2-ethylhexyl-4-(N,N dimethylamino)benzoate, N,N-dimethylaminoethyl methacrylate, ethyl 4-(N,N dimethylamino)benzoate, phosphite. Such a system is given, for example, by an organic peroxide in combination with an amine, in particular, an aromatic amine. For example, here, dibenzoyl peroxide or its derivatives with an aromatic amine such as, for example, 2,2'-(4-methylphenylimino)diethanol can be used. N,N-diethanol-p-toluidine, N,N-dimethyl-p-toluidine, N,N-dimethyl-sym-xylidine.

Additional particularly preferred radically polymerizable dental materials consist of a base paste A and initiator paste B and contain in component A or B one or more additives i) preferably buffer salts, dehydrators, metal scavengers, metal complex forming agents, further paste-forming agents, tensides, active ingredients, substances making optical sensing possible, flavor and/or fragrance substances that make diagnostics possible, tooth substance-corroding and/or adhesively acting substances such as, for example, MDP (methacryloyl decyl phosphate), fluoridation means, bleaching substances, desensitization agents, adhesive means, colorants, pigments, indicators, further initiators or initiator components, stabilizers, polymerization inhibitors, thixotropic aids and antibacterial substances or combinations of two or more thereof.

Particularly suited as paste forming agents j) are reactive paste forming agents that are aliphatic or cycloaliphatic compounds derived from maleic acid and/or fumaric acid, whereby these compounds have no further ethylenically unsaturated groups in addition to the groups derived from maleic acid and/or fumaric acid, and/or comprising the compounds, they are at least one allyl and/or methallyl residue that may have units derived from maleic acid and/or fumaric acid and which, in addition to the aforementioned ethylenically unsaturated groups, have no further ethylenically unsaturated groups.

In addition to or instead of the cited reactive paste forming agents, plasticizers or mixtures of plasticizers can be used as paste-forming agents. In general, these are plasticizers without ethylenically unsaturated groups. Examples of this are polyalkylene glycols or their derivatives such as their esters, for example, polyethylene glycols and their derivatives, polypropylene glycols and their derivatives or low-molecular, polyesters, as well as long-chained diesters of phthalic acid, such as dibutyl, dioctyl, dinonyl or diphenyl phthalate, or long-chained diesters of aliphatic dicarboxylic acids such as di(iso-nonyl adipate), or long-chained trialkyl phosphates, such as tricresyl phosphate, or esters of citric acid or aliphatic hydrocarbons or silicon oils that are liquid at 25° C.

As a rule, the percentage of ingredient a) in component A and/or B is 20 to 85% by weight, preferably 25-80% by weight and particularly preferred, 30 to 75% by weight. Preferred are polymerizable dental materials in which ingredient a) contains urethane-containing groups (meth)acrylate monomers having a percentage of ≥50% by weight, preferably ≥60% by weight, and particularly preferred ≥70% by weight.

The percentage of impact strength modifier compounds used in ingredients a) of component A and/or B is 0 to 20% by weight, preferably 0.5 to 15% by weight, particularly preferred 1 to 10% by weight.

As a rule, the percentage of the metal compound ingredient f) in component A is 1-100 ppm and preferably 2-50 ppm.

As a rule, the percentage of the halogenide and pseudohalogenide ingredient g) in component A is 0.01-1% by weight and preferably 0.05 to 0.5% by weight.

As a rule, the percentage of paste forming agent j) in component B is 10-85% by weight, preferably 20-80% by weight, particularly preferred, 30-75% by weight. Formulations without using paste forming agents j) in the initiator paste can be produced as well.

As a rule, the percentage of initiator and/or co-initiator e) in component A and/or B is 0.001-5% by weight and preferably 0.001-2% by weight.

As a rule, the percentage of the peroxide ingredient h) in component B is up to 5% by weight and preferably up to 2% by weight.

The percentage of the ingredient fused silica and/or cristobalite filler b) and of X-ray-opaque filler c) in component A and/or B is 15 to 80% by weight, preferably 20 to 80% by weight and particularly preferred 40 to 70% by weight.

The percentage of ingredient c) in component A and/or B is 0 to 50% by weight, preferably 0.1 to 30%, particularly, 15 to 25% by weight.

As a rule, the percentage of the ingredient barbituric acid/barbituric acid derivative/barbituric acid salt e) in component B is 0 to 15% by weight relative to the total mass of component B, preferably 1 to 10% by weight and particularly preferred, 2 to 5% by weight; as a rule, the percentage of ingredient e) in component A is 0 to 15% by weight relative to the total mass of component A, preferably 1 to 10% by weight and particularly preferred, 2 to 5% by weight.

The percentage of additional additives i) in component A and/or B is, as a rule, 0 to 20% by weight relative to the total mass of the respective component, preferably 0 to 15% and particularly preferred, 0 to 10% by weight.

Thereby, the weight information in the paragraphs above relate to the total mass of the relevant component A or B respectively.

The use of spatially separate pastes, i.e. of base paste (component A) and initiator paste (component B) prevents a premature formation of radicals during storage and thus the premature polymerization of the two components. Additionally, pastes are advantageous for handling the polymerizable dental material because it can then be mixed more carefully by hand and also by self-mixing systems (e.g. double cartridge with static or dynamic mixing tips), than is the case, for example, when using multicomponent systems that are based on powder and liquid.

The multicomponent composite according to the invention is processed by mixing the individual components of the previously described dental material into a polymerizable dental mass. Preferably, one base component A is mixed with a catalyst component B in a ratio of 1:2 to 20:1, particularly preferred, 1:1 to 10:1 and particularly preferred, 10:1, 5:1, 4:1, 2:1 and 1:1. These mixtures distinguish themselves by a quick polymerization in conditions present in the oral cavity.

The multicomponent system according to the invention is preferably stored in suitable primary packaging such as tubes, cans, and particularly preferred, in cartridges and pouches in the way they are stored and described, for example, in EP A 723,807, EP A 541,972, WO 98/44860 A1, EP A 492,412, EP A 492,413 and EP A 956,908, proportioned for subsequent use.

A special embodiment relates to the use of the polymerizable dental material described above, in particular, in the first embodiment, as dental material for the production of inlays, onlays, veneers, partial crowns, tooth fillings, artificial teeth, as material for models and for provisional and permanent crown and bridge material.

A further special embodiment relates to the use of the polymerizable dental material described above, in particular, in the second embodiment as dental material for producing core buildup material, as block and disk material for millable CAD-CAM restoration or as esthetic cement.

Particularly preferred, the dental material according to the invention is used for producing crown and bridge material or as core buildup material or as millable block and disc material for producing CAD-CAM designs or as esthetic cement, whereby this is to be understood as temporary and permanent provisional and definitive tooth replacement, or also for producing veneers, artificial teeth, inlays, onlays, partial crowns or tooth fillings, even indirectly by using CAD/CAM processes.

The invention also relates to a cured dental material that can be obtained by mixing the components A and B described above, advantageously at a ratio of 20:1 to 1:1, and by polymerization of the thereby obtained polymerizable dental material.

Refinements, advantages and possibilities of application of the invention are given by the following description of preferred exemplary embodiments. Thereby, all features described by themselves or in any reasonable combination constitute the subject matter of the invention, even independent of their summary in the individual claims and/or their reference.

The percentage information in the documents at hand is defined as percent by weight, unless specified otherwise.

Polymerized dental materials for the applications cited above require a high degree of stability, because the cured dental products according to the invention, due to the biting power to which the occlusion is subjected, for example, must be very strong to prevent breakage and also have a sufficiently stabilizing effect relative to the core of the teeth. As the result of integrating all ingredients into the polymerized dental material, significantly improved mechanical properties are achieved.

EXAMPLES

In the following examples, composite compounds according to the invention consisting of aliphatic monomer mixtures and cristobalite powder or mixtures consisting of cristobalite powder and fused silica are compared with comparative examples having partially aromatic monomer mixtures and a selection of various types of fillers. The technical data of the fillers used is summarized in the following table:

TABLE 1

Technical data of the fillers used (respectively silanized with 3-methacryloxypropyltrimethoxysilane).

| Filler | Grain size $d_{50\%}$ [μm] | BET surface area [m²/g] | Refractive index $n_d$ |
|---|---|---|---|
| Barium glass powder | 3 | 0.6 | 1.53 |
| Barium glass fine powder | 1.5 | 5 | 1.53 |
| Barium glass ultra-fine powder | 0.4 | 23 | 1.53 |
| Precipitated silicon dioxide | 4.5 | 55 | 1.46 |
| Pyrogenic silicon dioxide Aerosil R709 | n. a. | 35 | 1.46 |
| Cristobalite powder | 5 | 4 | 1.484-1.487[a] |
| Cristobalite fine powder | 2.5 | 8 | 1.484-1.487[a] |
| Cristobalite ultra-fine powder | 0.5 | 14 | 1.484-1.487[a] |
| Fused silica ultra-fine powder | 0.5 | 14 | 1.46 |
| Ytterbium floride, coated with SiO₂ | 0.1[b] | 3 | 1.53 |

[a] This is the refractive index of pure cristobalite that varies depending on the modification and the spatial direction.
[b] This states the size of the primary particles. The product is available as an agglomerated powder.

The solely chemically curing composites in the following comparative examples 1 through 7 and patent examples 1 through 5 are particularly suitable for producing temporary crowns and bridges, while the dual-curing composites in comparative example 8 and in patent example 6 are particularly suited as material for core buildup. For producing the base pastes, the ingredients indicated in the following tables 2 through 12 were homogenized and dispersed by a three-roll mill. For all base pastes produced, it was determined in preliminary tests as to which fill level would be required to obtain suitable viscosities (9 to 13 Pa·s at a shear ratio of $100\ s^{-1}$ and a temperature of 23° C.).

In all base paste formulations stated below, the viscosities are thus within this interval and can therefore be applied out of the conventional cartridges and double syringe systems by applying an easily manageable force.

TABLE 2

Production example of base paste I (not according to the invention)

| Ingredient | Amount [%] | Amount [g] |
|---|---|---|
| Ethoxylated Bisphenol A dimethacrylate (4EO) | 42.5 | 29.75 |
| Aliphatic urethane dimethylacrylate[1)I] | 13.5 | 9.45 |
| Barium fine powder 1.5 μm, methacryl-silanized | 36.6 | 25.62 |
| Pyrogenic silicon dioxide Aerosil DT4[2)] | 7.0 | 4.90 |
| 4-Hydroxyanisole | 0.1 | 0.07 |
| Copper(II)dimethacrylate in hydroxyethyl methacrylate (1% solution) | 0.1 | 0.07 |
| Dodecyltrimethyl ammonium chloride | 0.2 | 0.14 |

[I] Contains 24.1% by weight of urethane-group-containing (meth)acrylate monomers in the monomer mixture

TABLE 3

Production example of base paste II (not according to the invention)

| Ingredient | Amount [%] | Amount [g] |
|---|---|---|
| Ethoxylated Bisphenol A dimethacrylate (4EO) | 42.5 | 29.75 |
| Aliphatic urethane dimethylacrylate[1)II] | 13.5 | 9.45 |
| Barium ultra-fine powder 0.4 μm, methacryl-silanized | 36.6 | 25.62 |
| Pyrogenic silicon dioxide Aerosil DT4[2)] | 7.0 | 4.90 |
| 4-Hydroxyanisole | 0.1 | 0.07 |
| Copper(II)dimethacrylate in hydroxyethyl methacrylate (1% solution) | 0.1 | 0.07 |
| Dodecyltrimethyl ammonium chloride | 0.2 | 0.14 |

[II] Contains 24.1% by weight of urethane-group-containing (meth)acrylate monomers in the monomer mixture

TABLE 4

Production example of base paste III (not according to the invention)

| Ingredient | Amount [%] | Amount [g] |
|---|---|---|
| Ethoxylated Bisphenol A dimethacrylate (4EO) | 57.7 | 40.39 |
| Aliphatic urethane dimethylacrylate[1)III] | 18.3 | 12.81 |
| Precipitated silicon dioxide 4.5 μm[3)] | 23.5 | 16.45 |
| 4-Hydroxyanisole | 0.1 | 0.07 |
| Copper(II)dimethacrylate in hydroxyethyl methacrylate (1% solution) | 0.1 | 0.07 |
| Dodecyltrimethyl ammonium chloride | 0.2 | 0.14 |

[III] Contains 24.1% by weight of urethane-group-containing (meth)acrylate monomers in the monomer mixture

TABLE 5

Production example of base paste IV (not according to the invention)

| Ingredient | Amount [%] | Amount [g] |
|---|---|---|
| Ethoxylated Bisphenol-A dimethacrylate (4EO) | 56.6 | 39.63 |
| Aliphatic urethane dimethylacrylate[1)IV] | 18.0 | 12.59 |
| Pyrogenic silicon dioxide Aerosil R709[4)] | 25.0 | 17.50 |
| 4-Hydroxyanisole | 0.1 | 0.07 |
| Copper(II)dimethacrylate in hydroxyethyl methacrylate (1% solution) | 0.1 | 0.07 |
| Dodecyltrimethyl ammonium chloride | 0.2 | 0.14 |

[VI] Contains 24.1% by weight of urethane-group-containing (meth)acrylate monomers in the monomer mixture

TABLE 6

Production example of base paste V (not according to the invention)

| Ingredient | Amount [%] | Amount [g] |
|---|---|---|
| Ethoxylated Bisphenol A dimethacrylate (4EO) | 42.5 | 29.75 |
| Aliphatic urethane dimethylacrylate[1)V] | 13.5 | 9.45 |
| Cristobalite fine powder 2.5 µm methacryl-silanized | 36.6 | 25.62 |
| Pyrogenic silicon dioxide Aerosil DT4[2)] | 7.0 | 4.90 |
| 4-Hydroxyanisole | 0.1 | 0.07 |
| Copper(II)dimethacrylate in hydroxyethyl methacrylate (1% solution) | 0.1 | 0.07 |
| Dodecyltrimethyl ammonium chloride | 0.2 | 0.14 |

[V]Contains 24.1% by weight of urethane-group-containing (meth)acrylate monomers in the monomer mixture

TABLE 7

Production example of base paste VI (not according to the invention)

| Ingredient | Amount [%] | Amount [g] |
|---|---|---|
| Ethoxylated Bisphenol A dimethacrylate (4EO) | 42.5 | 29.75 |
| Aliphatic urethane dimethylacrylate[1)VI] | 13.5 | 9.45 |
| Cristobalite ultra-fine powder 0.5 µm methacryl-silanized | 36.6 | 25.62 |
| Pyrogenic silicon dioxide Aerosil DT4[2)] | 7.0 | 4.90 |
| 4-Hydroxyanisole | 0.1 | 0.07 |
| Copper(II)dimethacrylate in hydroxyethyl methacrylate (1% solution) | 0.1 | 0.07 |
| Dodecyltrimethyl ammonium chloride | 0.2 | 0.14 |

[VI]Contains 24.1% by weight of urethane group-containing (meth)acrylate monomers in the monomer mixture

TABLE 8

Production example of base paste VII (not according to the invention)

| Ingredient | Amount [%] | Amount [g] |
|---|---|---|
| Ethoxylated Bisphenol-A dimethacrylate (4EO) | 42.5 | 29.75 |
| Aliphatic urethane dimethylacrylate[1)VII] | 13.5 | 9.45 |
| Fused silica ultra-fine powder 0.5 µm methacryl-silanized | 36.6 | 25.62 |
| Pyrogenic silicon dioxide Aerosil DT4[2)] | 7.0 | 4.90 |
| 4-Hydroxyanisole | 0.1 | 0.07 |
| Copper(II)dimethacrylate in hydroxyethyl methacrylate (1% solution) | 0.1 | 0.07 |
| Dodecyltrimethyl ammonium chloride | 0.2 | 0.14 |

[VII]Contains 24.1% by weight of urethane-group-containing (meth)acrylate monomers in the monomer mixture

TABLE 9

Production example of base paste VIII (not according to the invention)

| Ingredient[VIII] | Amount [%] | Amount [g] |
|---|---|---|
| Bisphenol A glycidyl methacrylate | 20.4 | 10.20 |
| Triethylene glycol dimethacrylate | 13.6 | 6.80 |
| Barium glass powder 3 µm, methacryl-silanized | 58.6 | 29.30 |
| Pyrogenic silicon dioxide Aerosil DT4[2)] | 6.0 | 3.00 |
| 2,6-Di-tert-butyl-4-methylphenol | 0.04 | 0.02 |
| Camphor quinone | 0.13 | 0.07 |
| Ethyl 4-dimethylaminobenzoate | 0.13 | 0.07 |
| p-Tolyldiethanol amine | 1.1 | 0.55 |

[VIII]Contains 0% by weight of urethane-group-containing (meth)acrylate monomers in the monomer mixture

TABLE 10

Production example of base paste IX (according to the invention)

| Ingredient | Amount [%] | Amount [g] |
|---|---|---|
| Aliphatic urethane dimethylacrylate[1)IX] | 40.8 | 40.76 |
| 1,12-Dodecanediol dimethacrylate | 9.3 | 9.30 |
| Cristobalite ultra-fine powder 0.5 µm methacryl-silanized | 42.5 | 42.54 |
| Pyrogenic silicon dioxide Aerosil DT4[2)] | 7.0 | 7.00 |
| 4-Hydroxyanisole | 0.1 | 0.10 |
| Copper(II)dimethacrylate in hydroxyethyl methacrylate (1% solution) | 0.1 | 0.10 |
| Dodecyltrimethyl ammonium chloride | 0.2 | 0.20 |

[IX]Contains 81.4% by weight of urethane-group-containing (meth)acrylate monomers in the monomer mixture

TABLE 11

Production example of base paste X (according to the invention)

| Ingredient | Amount [%] | Amount [g] |
|---|---|---|
| Aliphatic urethane dimethylacrylate[1)IX] | 40.8 | 28.53 |
| 1,12-Dodecanediol dimethacrylate | 9.3 | 6.51 |
| Cristobalite ultra-fine powder 0.5 µm methacryl-silanized | 30.6 | 21.44 |
| Fused silica fine powder 0.5 µm methacryl-silanized | 11.9 | 8.34 |
| Pyrogenic silicon dioxide Aerosil DT4[2)] | 7.0 | 4.90 |
| 4-Hydroxyanisole | 0.1 | 0.07 |
| Copper(II)dimethacrylate in hydroxyethyl methacrylate (1% solution) | 0.1 | 0.07 |
| Dodecyltrimethyl ammonium chloride | 0.2 | 0.14 |

[X]Contains 81.4% by weight of urethane-group-containing (meth)acrylate monomers in the monomer mixture

TABLE 12

Production example of base paste XI (according to the invention)

| Ingredient | Amount [%] | Amount [g] |
|---|---|---|
| Aliphatic urethane dimethylacrylate[1)XI] | 40.8 | 28.53 |
| 1,12-Dodecanediol dimethacrylate | 9.3 | 6.51 |
| Cristobalite ultra-fine powder 0.5 µm methacryl-silanized | 28.4 | 19.93 |
| Fused silica fine powder 0.5 µm methacryl-silanized | 11.1 | 7.75 |
| Pyrogenic silicon dioxide Aerosil R709[4)] | 10.0 | 7.00 |
| 4-Hydroxyanisole | 0.1 | 0.07 |
| Copper(II)dimethacrylate in hydroxyethyl methacrylate (1% solution) | 0.1 | 0.10 |
| Dodecyltrimethyl ammonium chloride | 0.2 | 0.14 |

[XI]Contains 81.4% by weight of urethane-group-containing (meth)acrylate monomers in the monomer mixture

TABLE 13

Production example of base paste XII (according to the invention)

| Ingredient | Amount [%] | Amount [g] |
|---|---|---|
| Aliphatic urethane dimethylacrylate[1)XII] | 35.0 | 24.50 |
| 1,12-Dodecanediol dimethacrylate | 7.5 | 5.25 |
| Polytetramethylene glycol diacrylate[5)] | 7.0 | 4.90 |
| Cristobalite ultra-fine powder 0.5 µm methacryl-silanized | 28.9 | 20.23 |
| Fused silica ultra-fine powder 0.5 µm methacryl-silanized | 11.2 | 7.84 |
| Pyrogenic silicon dioxide Aerosil R709[4)] | 10.0 | 7.00 |
| 4-Hydroxyanisole | 0.1 | 0.07 |
| Copper(II)dimethacrylate in hydroxyethyl methacrylate (1% solution) | 0.1 | 0.07 |
| Dodecyltrimethyl ammonium chloride | 0.2 | 0.14 |

[XII]Contains 70.7% by weight of urethane-group-containing (meth)acrylate monomers in the monomer mixture

TABLE 14

Production example of base paste XIII (according to the invention)

| Ingredient | Amount [%] | Amount [g] |
| --- | --- | --- |
| Aliphatic urethane dimethylacrylate[1)XIII] | 24.00 | 12.00 |
| 1,12-Duodecanediol dimethacrylate | 6.0 | 3.00 |
| Cristobalite powder 0.5 μm methacryl-silanized | 42.6 | 21.30 |
| Ytterbium fluoride, coated with $SiO_2$, methacryl-silanized | 20.0 | 10.0 |
| Pyrogenic silicon dioxide Aerosil R709[4)] | 6.0 | 3.00 |
| 2,6-Di-tert-butyl-4-methylphenol | 0.04 | 0.02 |
| Camphor quinone | 0.13 | 0.07 |
| Ethyl 4-Dimethylaminobenzoate | 0.13 | 0.07 |
| p-Tolyldiethanol amine | 1.1 | 0.55 |

[XIII]Contains 80.0% by weight of urethane-group-containing (meth)acrylate monomers in the monomer mixture The initiator pastes were produced analogously to the base pastes. In this process, the ingredients listed in the following tables 15 and 16 were homogenized and dispersed using a three-roll mill.

TABLE 15

Production example of initiator paste I

| Ingredient | Amount [%] | Amount [g] |
| --- | --- | --- |
| Unsaturated polyester resin[6)] | 47.0 | 9.40 |
| Barium glass fine powder, unsilanized 1.5 μm | 41.5 | 8.30 |
| 1-Benzyl-5-phenyl barbituric acid | 8.0 | 1.60 |
| Pyrogenic silicon dioxide HDK ® H2000[7)] | 3.5 | 0.70 |

TABLE 16

Production example of initiator paste II

| Ingredient | Amount [%] | Amount [g] |
| --- | --- | --- |
| Unsaturated polyester resin[6)] | 47.0 | 9.40 |
| Cristobalite glass ultra-fine powder, unsilanized 0.5 μm | 41.5 | 8.30 |
| 1-Benzyl-5-phenyl barbituric acid | 8.0 | 1.60 |
| Pyrogenic silicon dioxide HDK ® H2000[7)] | 3.5 | 0.70 |

For base pastes VIII and XIII, the pertaining initiator pastes were produced in a manner analogous to the base pastes. In this process, the ingredients listed in the following tables 17 and 18 were homogenized and dispersed using a three-roll mill.

TABLE 17

Production example of initiator paste III (not according to the invention)

| Ingredient[XIV] | Amount [%] | Amount [g] |
| --- | --- | --- |
| Bisphenol A glycidyl methacrylate | 20.4 | 10.20 |
| Triethylene glycol dimethacrylate | 13.6 | 6.80 |
| Barium glass powder 3 μm, methacryl-silanized | 59.35 | 29.68 |
| Pyrogenic silicon dioxide DT4[2)] | 6.0 | 3.0 |
| 2,6-Di-tert-butyl-4-methylphenol | 0.05 | 0.03 |
| Dibenzoyl peroxide (75% in $H_2O$) | 0.60 | 0.30 |

[XVI]Contains 0% by weight urethane-group-containing (meth)acrylate monomers in the monomer mixture

TABLE 18

Production example of initiator paste IV (according to the invention)

| Ingredient | Amount [%] | Amount [g] |
| --- | --- | --- |
| Aliphatic urethane dimethyl acrylate[1)XV] | 24.0 | 12.00 |
| 1,12-Dodecanediol dimethacrylate | 6.0 | 3.00 |
| Cristobalite powder 5 μm, methacryl-silanized | 43.35 | 21.68 |
| Ytterbium fluoride coated with $SiO_2$, methacryl-silanized | 20.0 | 10.00 |
| Pyrogenic silicon dioxide Aerosil R709[4)] | 6.00 | 3.00 |
| 2,6-Di-tert-butyl-4-methylphenol | 0.05 | 0.03 |
| Dibenzoyl peroxide (75% in $H_2O$) | 0.60 | 0.30 |

[XV]Contains 80.0% by weight of urethane-group-containing (meth)acrylate monomers in the monomer mixture

[1)]The aliphatic urethane dimethacrylate is an isomer mixture consisting of di-2-methacryloxyethyl-2,2',4-trimethyl-hexamethylene dicarbamate and di-2-methacryloxyethyl-2,4,4'-trimethyl-hexamethylene dicarbamate.

[2)]The pyrogenic silicon dioxide Aerosil DT4 is a methacryl-silanized hydrophobic silicon dioxide that can be obtained under this name from Evonik Degussa GmbH, Frankfurt/Main, Germany.

[3)]The precipitated silicon dioxide 4.5 μm is the product Sipernat 350, which can be obtained from Evonik Degussa GmbH, Frankfurt/Main, Germany.

[4)]The pyrogenic silicon dioxide Aerosil R709 is a methacryl-silanized hydrophobic silicon dioxide that can be obtained under this name from Evonik Degussa GmbH, Frankfurt/Main, Germany.

[5)]Polytetramethyleneglycol acrylate is a compound with an average molecular weight of 750 g/mol.

[6)]The unsaturated polyester resin is a compound that was synthesized by using the components maleic anhydride, dipropylene glycol and 2-ethylhexanol, and which has an average molecular weight of $M_n = 650$ and $M_w = 1000$. An example of the structure is represented by the formula

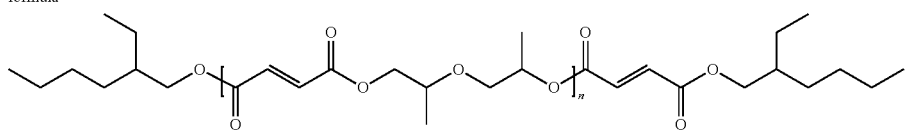

whereby some of the double bonds are also present in the cis form.

[7)]The pyrogenic silicon dioxide HDK ® H2000 is a pyrogenic silicon dioxide that has been subjected to surface modification with trimethyl-siloxy groups that has a carbon content of 2.5% and a specific BET surface area of 140 $m^2/g$ (according to DIN 66131 and DIN 66132), and is available under this name from Wacker-Chemie GmbH, Munich, Germany.

Subsequently, as per Table 19, the base pastes according to tables 2 through 8, as well as 10 through 13, were filled into the large chamber of a 10:1 cartridge of the type Mixpac CS 050-10-05 (Sulzer) with closure cap; the initiator pastes that were prepared according to tables 15 and 16 were filled into the small chamber in the same way. Thereby, the components listed in the following table consisting of base paste and initiator paste were filled which resulted in the comparative examples and patent examples. The base pastes according to Table 9 and 14 were filled into a chamber with a closure cap of a light-tight 1:1 double syringe of the type Mixpac SDL 010-01-52, in the same way, and the initiator pastes according to Tables 17 and 18 were filled into the other chamber analogously. The cartridges and double syringes were degassed by being centrifuged and closed air-tight with the respectively pertaining plungers.

TABLE 19

Overview of comparative examples and patent examples:

| Example | Base paste | Initiator paste |
|---|---|---|
| Comparative example 1 | I | I |
| Comparative example 2 | II | I |
| Comparative example 3 | III | I |
| Comparative example 4 | IV | I |
| Comparative example 5 | V | I |
| Comparative example 6 | VI | I |
| Comparative example 7 | VII | I |
| Comparative example 8 | VIII | III |
| Patent example 1 | IX | I |
| Patent example 2 | IX | II |
| Patent example 3 | X | II |
| Patent example 4 | XI | II |
| Patent example 5 | XII | II |
| Patent example 6 | XIII | IV |

For the analysis, the dental masses in the cartridges were applied by using a static mixer of the type Mixpac MBX 3.2-16-S (Sulzer); for the masses contained in the double syringes, a static mixer of the type Mixpac ML 2.5-08-S was used. Thereby, the modulus of elasticity and the flexural strength were determined (DIN EN ISO 10477:2004, traverse feed rate of 1 mm/min) using a Zwick Z010 Universal Test Machine running the software, TestXpert V11.02, or a Zwicki Universal Test Machine running the software, TestXpert II V3.41. The impact strength was tested using an identical test set-up, but in the case of comparative examples 1 through 7, and patent examples 1 through 5, at a transverse feed rate of 1.8 m/min and a Zwick Z1010 Universal Test Device running the software, TestXpert V11.02, and a telemetry rate of 100 Hz; and in the case of comparative example 8 and patent example 6, at a transverse feed rate of 2.0 m/min on a Zwicki Universal Testing Device running the software, TestXpert II V3.41, and a telemetry rate of 500 Hz. The measurements of the translucency and the opalescence were performed by using a Konica Minolta spectrometer of the type CM-3500d with a Xenon lamp as light source. The measurement of translucency (measurement of the relative transparency) was performed on a cured sample having a layer thickness of 2 mm. To measure the opalescence, a sample having a thickness of 2 mm in transmission as well as in reflection was examined with a spectral photometer in front of a black background. By using the L*a*b* values obtained from both measurements, a reference value for the opalescence was calculated according to the formula:

$$\text{Opalescence} = \sqrt{(a^*_{transm.} - a^*_{refl.})^2 + (b^*_{transm.} - b^*_{refl.})^2}$$

Additionally, in all examples, test personnel analyzed the surface gloss after having removed the inhibition layer with a dry paper tissue. For the dual-hardening materials of comparative example 8 and patent example 6, a light oven made by Schütz Dental of the type, Spektra LED, using an exposure time of 40 seconds was used for curing all test specimens. The results are shown in Table 20.

TABLE 20

Results of the cured products:

| Example | Fill level [%][i] | Modulus of Elasticity [MPa] | Flexural strength [MPa] | Impact strength [MPa] | Translucency | Opalescence | Gloss |
|---|---|---|---|---|---|---|---|
| Comparative example 1 | 43.18 | 3108 | 96 | 41 | 0.74 | 23.1 | − |
| Comparative example 2 | 40.63 | 2802 | 78 | 29 | 0.74 | 24.9 | + |
| Comparative example 3 | 23.66 | 1620 | 70 | 51 | 0.56 | 22.1 | − |
| Comparative example 4 | 25.59 | 1980 | 76 | 53 | 0.61 | 23.5 | + |
| Comparative example 5 | 42.90 | 3403 | 93 | 48 | 0.57 | 16.5 | − |
| Comparative example 6 | 42.46 | 3190 | 84 | 48 | 0.58 | 18.8 | + |
| Comparative example 7 | 42.35 | 3193 | 84 | 42 | 0.46 | 16.1 | + |
| Comparative example 8[ii] | 64.98 | 8043 | 120 | 38 | 0.74 | 19.1 | − |
| Patent example 1 | 47.57 | 2986 | 94 | 42 | 0.69 | 14.4 | + |
| Patent example 2 | 47.80 | 3350 | 92 | 48 | 0.69 | 18.0 | + |
| Patent example 3 | 47.65 | 3829 | 104 | 47 | 0.67 | 14.6 | + |
| Patent example 4 | 48.04 | 3788 | 99 | 49 | 0.64 | 17.6 | + |

TABLE 20-continued

Results of the cured products:

| Example | Fill level [%][i] | Modulus of Elasticity [MPa] | Flexural strength [MPa] | Impact strength [MPa] | Translucency | Opalescence | Gloss |
|---|---|---|---|---|---|---|---|
| Patent example 5 | 48.58 | 3465 | 101 | 60 | 0.64 | 17.2 | + |
| Patent example 6[iii] | 68.98 | 7464 | 146 | 98 | 0.60 | 20.2 | − |

[i] The fill level was determined experimentally by determining the annealing loss of the cured masses. The fill level resulting due to the inorganic proportion of the fillers (without silane) is calculated as follows: Fill level = 100 − annealing loss For typical commercial temporary crown and bridge materials, when compared with the Table above, the following percentage of inorganic filler is indicated: Luxatemp Star: 42.7% Luxatemp Automix Plus: 42.1% Protemp 4: 28.6% Structure Premium: 40.2% Structure 3: 23.5%
[ii] The translucency of typical core buildup materials is, as a rule, less than or close to 0.60. This is achieved by adding opaquing agents such as, for example, titanium dioxide. See the following examples: Luxacore Automix (A3): 0.56 Luxacore Z (white): 0.52 Multicore (light): 0.54 Rebilda DC (dentin): 0.60 Grandio Core Dual Cure (dentin): 0.54
[iii] The translucency of the uncolored mass of 0.60 is higher than that of the mix translucency of dentine and enamel of 0.56.
[ii],[iii] Additionally, the X-ray opaqueness of the dual-hardening materials is determined according to DIN EN ISO 4049:2010. In comparative example 8[ii], an X-ray opaqueness of 150 mm aluminum equivalent was found, in patent example 6[iii], of 200 mm aluminum equivalent.

Comparative example 1 describes a typical composite for a temporary crown and bridge material. As a result of the selection of monomers (refractive index of the mixture measured at 23° C. and a wavelength of 589 nm of 1.524) and fillers, high values are achieved for the modulus of elasticity and for the flexural strength at a relatively high fill level, the impact strength is average. The required translucency for esthetic tooth replacement masses should not have a value that is lower than 0.62 for the exemplary formulations without pigments that are listed here when subjected to the selected measurement conditions. This is ensured by comparative example 1. The opalescence is likewise high. Based on the relatively high average grain size $d_{50}$ of the glass filler particles of 1.5 μm, however, a glossy surface cannot be achieved with this material composition in the absence of a polishing step. As the result of using an X-ray-opaque dental glass, this composition is also relatively expensive.

In contrast to comparative example 1, comparative example 2 was produced with glass filler particles having an average grain size $d_{50}$ of 0.4 μm. In this example, it was possible to use the same fill amount as in comparative example 1 without a significant increase in viscosity, but due to the significantly higher percentage of silane in the fillers, the experimentally determined fill level is lowered. Due to the finer grinding, the values of the modulus of elasticity, the flexural strength and the impact strength are lowered significantly. However, this material composition exhibits a distinct surface gloss even without polishing after the inhibition layer has been removed. Because of the finer grinding of the fillers, the costs incurred relative to comparative example 1 are even higher.

In comparative example 3, a precipitated silicon dioxide was used as filler instead of the glass powder. In this case, due to the high BET surface area, only a low fill level is possible, the modulus of elasticity and the flexural strength are at a low level. However, the low fill level also ensures reduced brittleness and thus, relatively high levels of impact strength are achievable. However, based on the low level of translucency of 0.56, the material does not meet the requirements of high esthetics, and the large size of the aggregates of the filler particles results in a dull surface in the absence of polishing.

Also, when the pyrogenic silicon dioxide was used in comparative example 4, only a low fill level is possible for this class of materials in spite of the relatively low specific surface area. Compared with precipitated silicon dioxide, slightly improved mechanical stabilities are achieved which are, however, in light of the modulus of elasticity and the flexural strength, significantly lower than those of comparative example 1. On the other hand, the impact strength is higher. The translucency of 0.61 almost allows highly esthetic materials, the opalescence is very high. However, this material composition exhibits—even without polishing—a distinct surface gloss after the inhibition layer has been removed.

In comparative example 5, cristobalite powder with an average grain size $d_{50}$ of 1.5 μm was used as filler. In this case, good mechanical properties are achieved overall. Based on the low translucency of 0.57, the material does, however, not meet the requirements of high esthetics and the large aggregate size of the filler particles also leaves a dull surface in the absence of polishing.

In contrast to comparative example 5, comparative example 6 was produced with cristobalite filler particles having an average grain size $d_{50}$ of 0.4 μm. In this example, the same fill level as that in comparative example 5 could be achieved without a significant increase in viscosity. The values of the modulus of elasticity and flexural strength decrease only slightly. However, based on the low level of translucency of 0.58, the material does not meet the requirements of high esthetics. But this material composition shows, in contrast to comparative example 5, a distinct surface gloss after the inhibition layer has been removed, even in the absence of polishing.

In contrast to comparative example 6, comparative example 7 was produced with fused silica filler particles with an average grain size $d_{50}$ of 0.4 μm. With similar mechanical stabilities than those in comparative example 6, the translucency is reduced once again to 0.46. As a result, the material does not meet the requirements of high esthetics. However, even this material composition exhibits a distinct surface gloss even in the absence of polishing after the inhibition layer has been removed.

Comparative example 8 describes a typical composition for a core buildup material. By selecting monomers (refractive index in the mixture measured at 23° C. and at a wavelength of 589 nm of 1.511) and relatively coarse X-ray-opaque dental glasses, very high values of the modulus of elasticity and flexural strengths are achieved at a high fill level. The impact strength, however, is only average. As no opaquing agent (e.g. <0.05% titanium dioxide) was added, the translucency is comparatively high for a core buildup material. At 19.1, the opalescence is similar to that of a natural tooth. Based on the relatively high average grain size $d_{50}$ of the glass filler particles of 3 μm, however, it is not possible to achieve a glossy surface with this material composition without polishing, which is also not required for a core buildup material. Even though relatively expensive X-ray-opaque dental glass was used, a comparably moderate X-ray opaqueness of 150 mm Aluminium equivalent was achieved.

Instead of the monomer mixture used in the comparative examples, in patent example 1, a mixture consisting of aliphatic urethane dimethacrylate and 1,12-dodecanediol dimethacrylate was selected. The refractive index of this monomer mixture as measured at 23° C. and at a wavelength of 589 nm is 1.478. With a slightly lower modulus of elasticity and an improved flexural strength it was therefore possible, in contrast to comparative example 7, to achieve a translucency of 0.69, which already makes the production of highly esthetic crowns and bridges possible. Even this material composition exhibits a distinct surface gloss already after the inhibition layer is removed, even without any polishing.

In contrast to patent example 1, in patent example 2, cristobalite filler particles with an average granulate size $d_{50}$ of 0.4 μm was also used in the initiator paste. As a result, the modulus of elasticity and the flexural strength improve, even the opalescence increases—while translucency remains at a constant good level—as well as the property of surface gloss, even without any polishing.

In patent example 3, the cristobalite filler in the base paste was partially replaced with fused silica of the same average grain size. In this case, the modulus of elasticity and flexural strength rose significantly and the translucency of 0.67 is still sufficient for the production of highly esthetic crowns and bridges. This material composition also shows a distinct surface gloss after the inhibition layer is removed in the absence of any polishing.

In patent example 4, the pyrogenic silicon dioxide Aerosil DT4 was replaced with Aerosil R 709. With a slightly lower modulus of elasticity, flexural strength and also translucency, in this case, the opalescence increases. Also, this material composition once again shows a distinct surface gloss after the inhibition layer has been removed, even without polishing.

In contrast to patent example 4, in patent example 5, a low viscosity impact strength modifier (polytetramethylene glycol diacrylate) was added. At a lower modulus of elasticity, the impact strength thus significantly increases and is even above the values found in comparative example 3 and 4. The other properties remain unchanged.

In contrast to comparative example 8, in patent example 6, a mixture of aliphatic urethane dimethacrylate and 1,12-dodecanediol dimethacrylate was selected. The refractive index of this monomer mixture as measured at 23° C. and a wavelength of 589 nm is 1.478. With a slightly lower modulus of elasticity and an improved flexural strength, a significant increase in impact strength was found. A translucency of 0.60 is close to allowing highly esthetic materials, which adequately meets the requirements of core buildup materials. At 20.2, the opalescence is similar to that of a natural tooth. Based on the relatively large average grain size $d_{50}$ of the cristobalite filler particles of 5 μm, it is, however, not possible to achieve a glossy surface with this material composition without any polishing, which also is not required of a core buildup material. On account of the additional use of ytterbium fluoride, a higher X-ray opaqueness is achieved of 200 mm aluminum equivalent than in comparative example 8. Due to the use and the concentration of ytterbium fluoride, the costs are similar to those of comparative example 8 or more favorable. As is the case in the other patent examples, however, this formulation has the further advantage that it is free of monomers based on Bisphenol A.

What is claimed is:

1. A radically polymerizable dental material containing the components:
    a) at least one curable aliphatic and/or cycloaliphatic monomer system having a refractive index as measured at 23° C. and at a wavelength of 589 nm of less than or equal to 1.50, that contains at least one aliphatic and/or cycloaliphatic bis(meth)acrylate and/or at least one aliphatic and/or cycloaliphatic bis(meth)acrylamide in a mixture comprising aliphatic and/or cycloaliphatic bis(meth)acrylate monomers,
        wherein at least one of the monomers comprises one or several urethane groups, and at least one of the monomers does not comprise a urethane group,
            wherein the content of urethane-group-containing (meth)acrylate monomers in the monomer mixture is ≥50% by weight, relative to the monomer mixture, and
        wherein the monomer mixture contains 1 to 20% by weight relative to the total amount of component a) of low viscous (meth)acrylate and/or bis(meth)acrylate free of aromatic compounds, urethane groups and urea groups, having a viscosity of less than 2000 mPa·s as measured at a temperature of 23° C. with a cone/plate geometry of (35 mm, 4°), and a shear stress of 50 Pa,
    b) 15 to 80% by weight relative to the total mass of the dental material of at least one filler selected from the group of
        fused silica having a refractive index as measured at 23° C. and at a wavelength of 589 nm of 1.45 to 1.47, and
        cristobalite having a refractive index measured at 23° C. and at a wavelength of 589 nm of 1.48 to 1.49,
        or their combinations, and
    e) an initiator for radical polymerization,
    wherein the dental material contains in component a) 1 to 20% by weight relative to the total amount of the component a) of a polytetramethylene glycol di(meth)acrylate having an average molecular weight of 300 g/mol to 1000 g/mol, a viscosity of less than 2000 mPa·s as measured at a temperature of 23° C. with a cone/plate geometry of (35 mm, 4°) and a shear stress of 50 Pa, as an impact strength modifying (meth)acrylate monomer,
    provided, that the radically polymerizable dental material does not contain compounds comprising Bisphenol A groups.

2. The radically polymerizable dental material as recited in claim 1, wherein the at least one filler b) has an average grain size $d_{50}$ of between 0.2 and 1.0 μm as determined by means of sediment analysis.

3. The radically polymerizable dental material as recited in claim 1, wherein the dental material is devoid of radically polymerizable (meth)acrylates comprising aromatic groups.

4. The radically polymerizable dental material as recited in claim 1, wherein the dental material contains in component a) 1 to 20% by weight relative to the total amount of component a) of low viscous (meth)acrylate and/or bis(meth)acrylate that is free of aromatic compounds, urethane groups and urea groups, having a viscosity of less than 500 mPa·s as measured at a temperature of 23° C. with a cone/plate geometry of (35 mm, 4°), and a shear stress of 50 Pa.

5. The radically polymerizable dental material as recited in claim 1, wherein the filler b) is a mixture of fused silica and cristobalite.

6. The radically polymerizable dental material as recited in claim 1, wherein the at least one filler b) has an average grain size $d_{50}$ between 0.3 and 0.8 µm, and a surface area between 10 and 20 m²/g as determined according to BET.

7. The radically polymerizable dental material as recited in claim 1, further comprising d) nanoparticular fillers consisting of 0.1 to 15% by weight relative to the dental mass and having a BET surface area of 30 to 400 m²/g.

8. The radically polymerizable dental material as recited in claim 1, further comprising white, black, red and/or yellow organic or inorganic pigment.

9. The radically polymerizable dental material as recited in claim 1, wherein the dental material is present in the form of a two-component paste system consisting of base paste A and of an initiator paste B,
   wherein the base paste A has the following components:
      19 to 80% by weight relative to the total mass of base paste A consisting of a mixture of mono and multi-functional acrylates and/or methacrylates a) having a refractive index as measured at 23° C. and at a wavelength of 589 nm between 1.46 and 1.50,
      19 to 80% by weight relative to the total mass of base paste A of a cristobalite and/or fused silica b), having an average grain size $d_{50}$ of 0.3 to 0.8 µm, and a specific surface area of 10 to 20 m²/g as determined according to the BET method,
         wherein the cristobalite has a refractive index as measured at 23° C. and at a wavelength of 589 nm of 1.484 to 1.487, and the fused silica has a refractive index at 23° C. and at a wavelength of 589 nm of 1.455 to 1.465,
      1 to 15% by weight relative to the total mass of base paste A of a fumed silica d) having a specific surface area of 30 to 400 m²/g as determined according to the BET method,
      at least one metal compound f),
      at least one halogenide and/or pseudohalogenide compound g), and
      optionally, one or more photoinitiators and/or photo co-initiators e),
   wherein the initiator paste B contains the following components:
      19 to 80% by weight relative to the total mass of the initiator paste B of a paste-forming agent j) having a refractive index at 23° C. and at a wavelength of 589 nm between 1.460 and 1.520,
      0 to 80% by weight relative to the total mass of the initiator paste B of a cristobalite and/or fused silica b), having an average grain size $d_{50}$ of 0.3 to 0.8 µm, and a specific surface area of 10 to 20 m²/g as determined according to the BET method,
         wherein the fused silica has a refractive index at 23° C. and at a wavelength of 589 nm of 1.455 to 1.465, and wherein the cristobalite has a refractive index at 23° C. and at a wavelength of 589 nm of 1.484 to 1.487,
      0 to 80% by weight relative to the total mass of the initiator paste B of other conventional dental fillers with the exception of fused silica and cristobalite,
      1 to 15% by weight relative to the total mass of the initiator paste B of a barbituric acid derivative and/or a malonyl sulfamide e), and
      0 to 2% by weight relative to the total mass of initiator paste B of an organic peroxygen compound h), and optionally, one or several photo hardening initiators and/or photo co-initiators e).

10. The radically polymerizable dental material as recited in claim 1, wherein the dental material is present in the form of a pasty two-component system consisting of base paste A and of initiator paste B,
    wherein the base paste A contains the following components:
       18.99 to 80% by weight relative to the total mass of the base paste A of a mixture consisting of mono-functional and multifunctional acrylates and/or methacrylates a) that have a refractive index at 23° C. and at a wavelength of 589 nm between 1.46 and 1.50,
       18.99 to 80% by weight relative to the total mass of the base paste A of a cristobalite and/or fused silica b), having an average grain size $d_{50}$ of 0.3 to 0.8 µm, and a specific surface area of 10 to 20 m²/g as determined according to the BET method,
          wherein the cristobalite has a refractive index at 23° C. and at a wavelength of 589 nm of 1.484 to 1.487, and the fused silica has a refractive index at 23° C. and at a wavelength of 589 nm of 1.455 to 1.465,
       1 to 15% by weight relative to the total mass of the base paste A of a fumed silica d) having a specific surface area of 30 to 400 m²/g as determined according to the BET method, and
       0.01 to 2% by weight relative to the total mass of base paste A of an amine,
       and optionally one or several photoinitiators and/or additional co-initiators e), and
    wherein the initiator paste B contains the following components:
       19.99 to 80% by weight relative to the total mass of the initiator paste B of a mixture consisting of monofunctional and multifunctional acrylates and/or methacrylates a) that have a refractive index at 23° C. and at a wavelength of 589 nm between 1.46 and 1.50,
       19.99 to 80% by weight relative to the total mass of the initiator paste B of a cristobalite and/or fused silica b) that has an average grain size $d_{50}$ of 0.3 to 0.8 µm, as well as a specific surface area of 10 to 20 m²/g as determined according to the BET method,
          wherein the fused silica has a refractive index at 23° C. and at a wavelength of 589 nm of 1.455 to 1.465, and wherein the cristobalite has a refractive index at 23° C. and at a wavelength of 589 nm of 1.484 to 1.487,
       0.01 to 2% by weight relative to the total mass of the initiator paste B, of at least one organic peroxide h), and
       optionally, one or several photoinitiators and/or co-initiators e).

11. A cured dental material that is obtainable by curing the radically polymerizable dental material as recited in claim 1.

12. The cured dental material as recited in claim 11, wherein the dental material has a resistance to impact of at least 55 MPa.

13. The cured dental material as recited in claim 12, wherein the dental material has a flexural strength of at least 90 MPa and/or a translucence of at least 0.60.

14. A method for producing inlays, onlays, veneers, partial crowns, tooth fillings, artificial teeth, and model material for provisional crown, permanent crown and bridge material, the method comprising curing the polymerizable dental material as recited in claim 1.

15. A method for producing core buildup material, block and disc material for millable CAD-CAM restorations or for esthetic cement, the method comprising curing the polymerizable dental material as recited in claim 1.

16. The radically polymerizable dental material as recited in claim 5, wherein the weight ratio of fused silica to cristobalite is of 1:1 to 10.

17. A cured dental material obtained by curing the radically polymerizable dental material as recited in claim 9, wherein base paste A and initiator paste B are present at a ratio of 20:1 to 1:1.

18. A cured dental material obtained by curing the radically polymerizable dental material as recited in claim 10, wherein base paste A and initiator paste B are present at a ratio of 20:1 to 1:1.

19. A radically polymerizable dental material containing the components:
   a) at least one curable aliphatic and/or cycloaliphatic monomer system having a refractive index at 23° C. and at a wavelength of 589 nm that is less than or equal to 1.50, that contains at least one aliphatic and/or cycloaliphatic bis(meth)acrylate and/or at least one aliphatic and/or cycloaliphatic bis(meth)acrylamide,
   b) 15 to 80% by weight relative to the total mass of the dental material of at least one filler selected from the group of
      fused silica having a refractive index at 23° C. and at a wavelength of 589 nm of 1.45 to 1.47, and
      cristobalite having a refractive index at 23° C. and at a wavelength of 589 nm of 1.48 to 1.49,
      or their combinations, and
   c) 5 to 50% by weight relative to the total mass of the dental material of an X-ray-opaque filler c) that contains an irregularly shaped or spherical $YbF_3$— or $YF_3$-powder having an average grain size of the primary particles of 40 nm to 1.5 μm, which is a core/shell combination product consisting of $YF_3$— or $YbF_3$-core and $SiO_2$ shell, wherein the $SiO_2$ shell surface is silanized,
   provided that the radically polymerizable dental material does not contain compounds comprising Bisphenol A groups.

20. The radically polymerizable dental material as recited in claim 19, wherein component a) contains at least one aliphatic and/or cycloaliphatic bis(meth)acrylate and/or at least one aliphatic and/or cycloaliphatic bis(meth)acrylamide in a mixture comprising aliphatic and/or cycloaliphatic bis(meth)acrylate monomers
   wherein at least one of the monomers comprises one or several urethane groups, and at least one of the monomers does not comprise a urethane group,
      wherein the content of urethane-group-containing (meth)acrylate monomers in the monomer mixture is 50% by weight, relative to the monomer mixture, and
      wherein the monomer mixture contains 1 to 20% by weight relative to the total amount of component a) of low viscous (meth)acrylate and/or bis(meth)acrylate free of aromatic compounds, urethane groups and urea groups having a viscosity of less than 2000 mPa·s as measured at a temperature of 23° C. with a cone/plate geometry (35 mm, 4°), and a shear stress of 50 Pa.

21. The radically polymerizable dental material as recited in claim 19, wherein the dental material contains no radically polymerizable (meth)acrylates comprising aromatic groups.

22. The radically polymerizable dental material as recited in claim 19, wherein the dental material is present in the form of a pasty two-component system consisting of base paste A and of initiator paste B,
   wherein the base paste A contains the following components:
      13.99 to 80% by weight relative to the total mass of the base paste A of a mixture consisting of mono-functional and multifunctional acrylates and/or methacrylates a) that have a refractive index at 23° C. and at a wavelength of 589 nm between 1.46 and 1.50,
      13.99 to 80% by weight relative to the total mass of the base paste A of a cristobalite and/or fused silica b) that has an average grain size $d_{50}$ of 0.8 to 20 μm, and a specific surface area of 1.0 to 20 $m^2/g$ as determined according to the BET method,
         wherein the cristobalite has a refractive index at 23° C. and at a wavelength of 589 nm of 1.484 to 1.487, and the fused silica has a refractive index at 23° C. and at a wavelength of 589 nm of 1.455 to 1.465,
      5 to 30% by weight relative to the total mass of the base paste A of an X-ray-opaque additive c) consisting of an irregularly shaped or spherical $YbF_3$— or $YF_3$— powder having an average grain size of the primary particles of 40 nm to 1.5 μm, which is a core/shell combination product consisting of a $YF_3$— or $YbF_3$— core and a $SiO_2$ shell, wherein the $SiO_2$ shell surface is silanized,
      1 to 15% by weight relative to the total mass of the base paste A of a nanoscale silicon dioxide and/or $SiO_2$ d) that is present in the form of primary particles, clusters, aggregates and/or agglomerates having a specific surface area of 30 to 400 $m^2/g$ as determined according to the BET method, and
      0.01 to 2% by weight relative to the total mass of the base paste A of an amine, and
      optionally, one or several photoinitiators and/or additional co-initiators e), and
   wherein the initiator paste B contains the following components:
      13.99 to 80% by weight relative to the total mass of the initiator paste B of a mixture consisting of monofunctional and multifunctional acrylates and/or methacrylates a) that have a refractive index at 23° C. and at a wavelength of 589 nm between 1.46 and 1.50,
      13.99 to 80% by weight relative to the total mass of the initiator paste B of a cristobalite and/or fused silica b) that has an average grain size $d_{50}$ of 0.8 to 20 μm, and a specific surface area of 1.0 to 20 $m^2/g$ as determined by the BET method,
         wherein the cristobalite has a refractive index at 23° C. and at a wavelength of 589 nm of 1.484 to 1.487, and the fused silica has a refractive index at 23° C. and at a wavelength of 589 nm of 1.455 to 1.465,
      5 to 30% by weight relative to the total amount of the initiator paste B of X-ray-opaque additives c) that are irregularly shaped or spherical $YbF_3$— or $YF_3$— powders having an average grain size or primary particle size of 40 nm to 1.5 μm, which is a combination product consisting of a $YF_3$— or $YbF_3$— core and a $SiO_2$ shell, wherein the $SiO_2$ shell surface is silanized,
      1 to 15% by weight relative to the total mass of the initiator paste B of a nanoscale silicon oxide and/or $SiO_2$ d) that is present in the form of primary particles, clusters, aggregates and/or agglomerates having a specific surface area of 30 to 400 $m^2/g$ as determined according to the BET method,
      0.01 to 2% by weight relative to the total mass of the initiator paste B of at least one organic peroxide h), and
      optionally, one or several photoinitiators and/or photo co-initiators e).

23. The radically polymerizable dental material as recited in claim 19, wherein
the average grain size $d_{50}$ of the at least one filler b) is between 1.0 and 50 μm as determined by using a laser refraction particle size measurement device Malvern Mastersizer 3000 with Hydro MV dispersion unit, and
the dental material contains 5 to 50% by weight relative to the total mass of the dental material of an X-ray-opaque filler c) that contains an irregularly shaped or spherical $YbF_3$— or $YF_3$— powder having an average grain size of the primary articles of 40 nm to 1.5 μm, which is a core/shell combination product consisting of a $YF_3$— or $YbF_3$-core and a $SiO_2$ shell, wherein the $SiO_2$ shell surface is silanized.

24. The radically polymerizable dental material as recited in claim 19, wherein the dental material contains as component a) a mixture consisting of aliphatic and/or cycloaliphatic bis(meth)acrylate monomers,
wherein at least one of the monomers comprises one or several urethane groups, and at least one of the monomers does not comprise a urethane group.

25. The radically polymerizable dental material as recited in claim 19, wherein
the average grain size $d_{50}$ of the at least one filler b) is between 1.0 and 20 μm, and
the surface area of the at least one filler b) as determined according to BET is between 2 and 6 $m^2/g$.

26. A cured dental material that is obtained by curing the radically polymerizable dental material as recited in claim 19.

27. A cured dental material obtained by curing the radically polymerizable dental material as recited in claim 22, wherein base paste A and initiator paste B are present at a ratio of 20:1 to 1:1.

28. A method for producing inlays, onlays, veneers, partial crowns, tooth fillings, artificial teeth, and model material for provisional crown, permanent crown and bridge material, the method comprising curing the polymerizable dental material as recited in claim 19.

29. A method for producing core buildup material, block and disc material for millable CAD-CAM restorations or for esthetic cement, the method comprising curing the polymerizable dental material as recited in claim 19.

* * * * *